United States Patent
Lafaquiere et al.

(10) Patent No.: US 11,512,293 B2
(45) Date of Patent: Nov. 29, 2022

(54) USE OF TYPE III POLYKETIDE SYNTHASES AS PHLOROGLUCINOL SYNTHASES

(71) Applicant: COMPAGNIE GENERALE DES ETABLISSEMENTS MICHELIN, Clermont-Ferrand (FR)

(72) Inventors: Vincent Lafaquiere, Clermont-Ferrand (FR); Odile Ramaen, Ablis (FR); Dominique Louis, Forges les Bains (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 13 days.

(21) Appl. No.: 16/627,707

(22) PCT Filed: Jun. 29, 2018

(86) PCT No.: PCT/FR2018/051618
§ 371 (c)(1),
(2) Date: Dec. 30, 2019

(87) PCT Pub. No.: WO2019/002798
PCT Pub. Date: Jan. 3, 2019

(65) Prior Publication Data
US 2020/0123508 A1 Apr. 23, 2020

(30) Foreign Application Priority Data
Jun. 30, 2017 (FR) ..................................... 1756108

(51) Int. Cl.
*C12P 7/22* (2006.01)
*C12N 9/10* (2006.01)
*C12N 15/81* (2006.01)
*C12N 15/90* (2006.01)

(52) U.S. Cl.
CPC ........... *C12N 9/1029* (2013.01); *C12N 15/81* (2013.01); *C12N 15/90* (2013.01); *C12P 7/22* (2013.01)

(58) Field of Classification Search
CPC .................................. C12N 9/1029; C12P 7/22
See application file for complete search history.

(56) References Cited

U.S. PATENT DOCUMENTS

| 10,179,921 B2* | 1/2019 | Delage ................. C12N 9/1029 |
| 2007/0178571 A1 | 8/2007 | Frost |
| 2014/0315269 A1 | 10/2014 | Delage et al. |

FOREIGN PATENT DOCUMENTS

WO 2012/003461 A2 1/2012

OTHER PUBLICATIONS

Siberfeld et al., Cryptogamie, Algologie, 35(2), 117-156, 2014.*
J. Achkar et al., "Biosynthesis of Phloroglucinol," J. Am Chem Soc., vol. 127, pp. 5332-5333 (2005).
L. Meslet-Cladière et al., "Structure/Function Analysis of a Type III Polyketide Synthase in the Brown Alga Ectocarpus siliculosus Reveals a Biochemical Pathway in Phlorotannin Monomer Biosynthesis," The Plant Cell, vol. 25, pp. 3089-3103 (2013).
W. Zha et al., "Characterization of the Substrate Specificity of PhlD, a Type III Polyketide Synthase from Pseudomonas fluorescens," J. Biol Chem., vol. 281, No. 42, pp. 32036-32047 (2006).
I. Abe et al., "Engineered Biosynthesis of Plant Polyketides: Chain Length Control in an Octaketide-Producing Plant Type III Polyketide Synthase," J. Am. Chem. Soc., vol. 127, pp. 12709-12716 (2005).
H. Baharum et al., "Molecular Cloning, Modeling, and Site-Directed Mutagenesis of Type III Polyketide Synthase from Sargassum binderi (Phaeophyta)," Marine Biotechnology, vol. 13, No. 5, pp. 845-856 (2011).
S. Sasso et al., "Microalgae in the postgenomic era: a blooming reservoir for new natural products," FEMS Microbiol. Rev., pp. 1-25 (2011).
Database UniProt XP002780083, "SubName: Full=Uncharacterized protein {ECO:0000313 | EMBL:EGB09027.1}", retrieved from EBI accession No. UNIPROT:F0Y6J5 (2011).
Database UniProt XP002780084, "SubName: Full=Type III polyketide synthase {ECO:0000313 | EMBL:ADK13089.1}", retrieved from EBI accession No. UNIPROT:D9J215 (2010).
Database EMBL XP002780085, "Sargassum binderi type III polyketide synthase mRNA, complete cds.", retrieved from EBI accession No. EM_STD:HM245964 (2010).
Database UniProt XP002780022, "SubName: Full=Long-chain alpha-pyrone synthase {ECO:0000313 | EMBL:SDQ98350.1}", retrieved from EBI accession No. UNIPROT:A0A1H1FBR5 (2017).
Database UniProt XP002780023, "SubName: Full=Polyketide synthase {ECG:0000313 | EMBL:KXP15269.1}", retrieved from EBI accession No. UNIPROT:A0A138AXW3 (2016).
Database UniProt XP002780024, "polyketide synthase [Tsukamurella tyrosinosolvens]", retrieved from NCBI accession No. RefSeq:WP_068743031.1 (2016).
Co-Pending U.S. Appl. No. 16/627,712, filed Jun. 29, 2018.
International Search Report dated Sep. 7, 2018, in corresponding PCT/FR2018/051618 (8 pages).
M.N. Mandryk-Litvinkovich et al., "Molecular Genetic Analysis of Determinants Defining Synthesis of 2,4-Diacety/phloroglucinol by Pseudomonas brassicacearum BIM B-446 Bacteria", Applied Biochemistry and Microbiology, 53(1), pp. 31-39 (2017).
J.K. Patel et al., "Engineered production of 2,4-diacetylphloroglucinol in the diazotrophic endophytic Bacterium pseudomonas sp. WS5 and its beneficial effect in multiple plant-pathogen systems", Applied Soil Ecology, 124, pp. 34-44 (2017).

(Continued)

*Primary Examiner* — Maryam Monshipouri
(74) *Attorney, Agent, or Firm* — Venable LLP

(57) ABSTRACT

Methods for producing phloroglucinol as well as methods of using type III polyketide synthases as phloroglucinol synthases, in particular the type III polyketide synthases of algae, such as eukaryotic ochrophyte algae, are described herein. In addition, polypeptides that have phloroglucinol synthase activity, the isolated nucleic acid molecules encoding these type III polyketide synthases, and the vectors and the host cells comprising such nucleic acid molecules are also described.

20 Claims, 12 Drawing Sheets

Specification includes a Sequence Listing.

(56) References Cited

OTHER PUBLICATIONS

J. Almario et al., "Distribution of 2,4-Diacetylphloroglucinol Biosynthetic Genes Among *Pseudomonas* spp. Reveals Unexpected Polyphyleism", Frontiers in Microbiology, 8, Article 1218 (2017).

D. Yu et al., "Type III Polyketide Synthases in Natural Product Biosynthesis", IUBMB Life, 64(4), pp. 285-295 (2012).

Extract from France Terme of French Ministry of Culture, http://www.culture.fr/franceterme/result?francetermeSearchTerme+cellule+h%C3%B4te&frnacetermeSearchDomaine=0&francetermeSearchSubmit=search&action=search (2000).

Extract from Biology-online.org for "host cell" (2008), retrieved Jun. 8, 2021.

M. B. Austin, et al., "The chaicone synthase superfamily of type III polyketide synthases", Nat. Prod. Rep., vol. 20, pp. 79-110 (2003).

Y. Shimizu, et al., "Discriminating the reaction types of plant type III polyketide synthases", Bioinformatics, vol. 33, No. 13, pp. 1937-1943 (2017).

Polyketide synthase [Tsukamurella tyrosinosolvens], htttps://www.ncbi.nlm.nih.gov/protein/WP_068743031.?report=genpept (retrieved Jan. 18, 2022).

\* cited by examiner

Fig. 1

```
                            10         20         30         40         50         60         70         80         90
                            |....|....|....|....|....|....|....|....|....|....|....|....|....|....|....|....|....|....|
PhlD.Pf  [P. protegens Pf-5]       ................................MSTLCLPHVMFPQHKITQQQMVDHLENLHADHPRMALAKRMIANTEVNE  49
PHLD.Es  [E. siliculosus]    MS-----------------------------KDEQTVYPVIAGMAIGNPQYRCTQNEALAVASKCPGLESIKPVLERIYGNSRIGS  57
PHLD.Sbi [S. binderi]        MSSAAVAMLADPTVQIALACIVLSLIVVFRSYRKGKDEQTVYPVIAGMAIGNPQYRCTQDQALTVAQKCPGVESVKPVLERIYGNSRIGS  90
PHLD-1.Aa [A. anophagefferens] MS-----------------------------KKDEKIIPVIMGMATGNPPYRASQQQALAIAESCPECNSIKPVLARIYGNSRIDY  57

100        110        120        130        140        150        160        170        180
                            |....|....|....|....|....|....|....|....|....|....|....|....|....|....|....|....|....|....|
PhlD.Pf  [P. protegens Pf-5]  RHIVLPIDELAVHT----------GFTHRSIVYEREARQMSSAAARQAIENAGLQISDIRMVIVTSCTGFMPSLTAHLINDLAL 124
PHLD.Es  [E. siliculosus]    RYFAVPDFTPGRAAKGDPLFYPADGSYQVPVDVRLDKFKEKAVPLVSDVARRAIKEAGLNVEDISKLVVVSSTGFLGPGLDCELIKNLGL 147
PHLD.Sbi [S. binderi]        RYFAVPDFTPNQAAKGDPMFFPADGSFEVPVDTRLDKFKEKAVPLVSDVARRAIKEAGIDVSKLVVVSSTGFLGPGLDCELIKNLGL 180
PHLD-1.Aa [A. anophagefferens] RFMAVPDFTPEQKLEGDENFFDKDLMFKMPVEKRLDMFREKSVPLVTKVCKDAMADAGIDVEQIGKLVVVSSTGFLGPGLDAELIKTLGL 147

190        200        210        220        230        240        250        260        270
                            |....|....|....|....|....|....|....|....|....|....|....|....|....|....|....|....|....|....|
PhlD.Pf  [P. protegens Pf-5]  PTSTVQLPIAQLGCVAGAAAINRANDFARLDARNHVLIVSLEFSSLCYQPDDTKLHAFISAALFGDAVSACVLR------ADDQAGGFKIK 209
PHLD.Es  [E. siliculosus]    TRSVDRTLIGFMGCAAAMNGFRNANDYVTANPGKYALMICVELSSVHT-TFDDNINDAILHAIFADGCAAAVLKGARK-SECPKGTLAIV 235
PHLD.Sbi [S. binderi]        TRSVDRTLIGFMGCAAAMNGFRNANDFVTANPGKYALMICVELSSVHT-TFDDNINDAILHAIFADGCAAAVLKGVRK-SEAPKGTLAIV 268
PHLD-1.Aa [A. anophagefferens] WRGVDRSLIGFMGCAAAMNGFRVANDFAMSHPGKMALMVCVEISSVHT-TFDDNVNDAILHAIFADGCAAAVISGEKPGSAAAKGKFGIV 236

280        290        300        310        320        330        340        350        360
                            |....|....|....|....|....|....|....|....|....|....|....|....|....|....|....|....|....|....|
PhlD.Pf  [P. protegens Pf-5]  KTESYFLPKSEHYIKYDVKDTGFHFTLDKAVMNSIKD-VAPVMERLNYESFEQNCAHNDFFIFHTGGRKILDELVMHLDLASNRVSQSRS 298
PHLD.Es  [E. siliculosus]    DNHAWLMEGTEDGITLAIKPNGITCTLSKFLPQYIAKNIAFFADGFLKKEK-LGRDDVDFWCVHPGGRRIIEEAQNGLGLSEEQTADSWA 324
PHLD.Sbi [S. binderi]        DNHAWLMEGTEDGITLAIKPNGITCTLSKFLPQYIAKNIAFFADGFLKKHN-LGRDDVDFWCVHPGGRRIIEEAQNGLGLTEAQTADSWA 357
PHLD-1.Aa [A. anophagefferens] DTHGWLMEGTEDGITLSINENGISCILSKYLPQYIAKNMAGYVDSFLGMHG-LQKTDMDFWAIHPGGRRIIEEAQNGLGLSEEQAKYSWT 325

370        380        390        400        410
                            |....|....|....|....|....|....|....|....|....|....|
PhlD.Pf  [P. protegens Pf-5]  SLSEAGNIASVVVFDVLKRQFDSN------LNRGDIGLLAAFGPGFTAEMAVGEWTA 349
PHLD.Es  [E. siliculosus]    VLGEYGNMLSPSVMFVLSRVFKRHNAALAQGKPGYQTGMAFSFSPGVGAEGILLRQI- 381
PHLD.Sbi [S. binderi]        VLAEYGNMLSPSVMFVLSRVFKRHNAALAQGKPGYQTGMAFSFSPGVGAEGILLRQI- 414
PHLD-1.Aa [A. anophagefferens] VLSQIYGNMLSPSVMFVLELILNDHKKALAKGERGLKQGIAFSFSPGVGAEGILINVM- 382
```

Fig. 4

Fig. 8A
| Gene | phloroglucinol mg.l$^{-1}$ | OD$_{600nm}$ | number of copies | Phloroglucinol /copy (mg.l$^{-1}$) |
|---|---|---|---|---|
| PHLD.Pf | 0 | 50 | 7 | 0 |
| PKS1.Es | 64 | 51 | 9 | 7 |
| PHLD.Sbi | 440 | 30 | 27 | 17 |
| PHLD.Aa | 0 | 51 | 26 | 0 |
| PHLD-1.Aa | 225 | 68 | 11 | 20 |
Fig. 8B
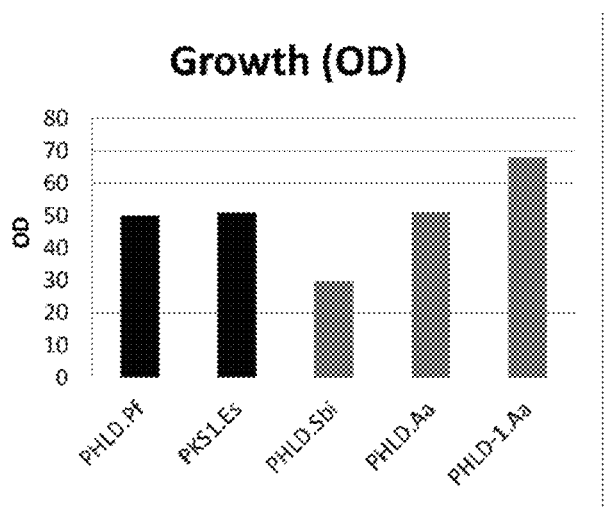
Fig. 8C
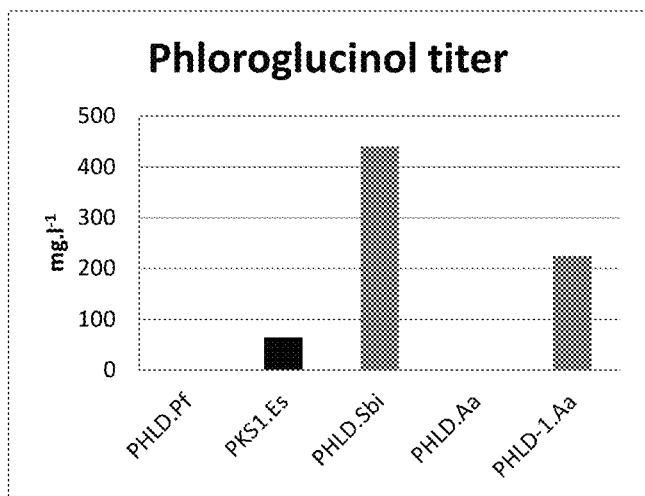

| PHLD | phloroglucinol mg.l⁻¹ | | OD 600nm | PHLD gene copy number |
|---|---|---|---|---|
| | mean | standard deviation | | |
| pADH2-PHLD.Pf | 0.0 | 0.0 | 54 | 1 |
| pADH2-PKS1.Es | 2.7 | 1.0 | 57 | 1 |
| pADH2-PHLD.Sbi | 11.8 | 7.1 | 58 | 1 |
| pADH2-PHLD-1.Aa | 6.9 | 4.3 | 55 | 1 |

| PHLD | phloroglucinol mg.l$^{-1}$ | | OD 600nm | PHLD gene copy number |
|---|---|---|---|---|
| | mean | standard deviation | | |
| pCCW12-PHLD.Pf | 0.0 | 0.0 | 57 | 1 |
| pCCW12-PKS1.Es | 8.4 | 2.7 | 57 | 1 |
| pCCW12-PHLD.Sbi | 21.6 | 7.8 | 58 | 1 |
| pCCW12-PHLD-1.Aa | 16.1 | 3.4 | 58 | 1 |

USE OF TYPE III POLYKETIDE SYNTHASES AS PHLOROGLUCINOL SYNTHASES

FIELD OF THE INVENTION

The present invention lies in the fields of microbial biochemistry and more particularly in the field of the synthesis of phloroglucinol by microbial enzymes. It relates to the use of type III polyketide synthases as phloroglucinol synthases, in particular type III polyketide synthases of algae, preferably of eukaryotic ochrophyte algae.

BACKGROUND

Phloroglucinol is an aromatic organic compound used in particular in the production of pharmaceutical products and explosives.

Phloroglucinol synthesis is catalysed by type III polyketide synthases known as phloroglucinol synthases. Phloroglucinol synthases carry out the condensation of three malonyl-CoA molecules so as to form a phloroglucinol molecule according to the following reaction scheme (Reaction I):

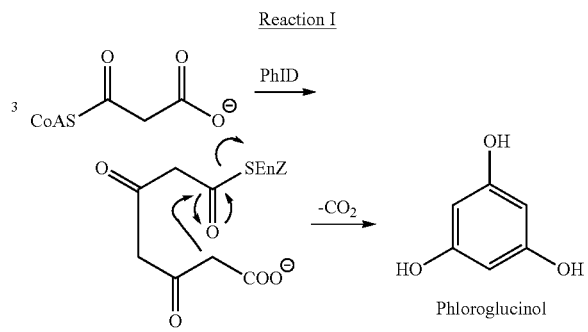

Numerous oligomers can subsequently be synthesized from phloroglucinol, such as phlorotannins. Phlorotannins include in particular fucols, phloretols and fucophloretols, which are phloroglucinol-derived products that make up the wall of brown algae. In addition, various protective activities of brown algae have also been attributed to phlorotannins.

At the current time, phloroglucinol synthesis has been described only in Gram-*Pseudomonas fluorescens* bacteria (Achkar et al., 2005; Zha et al., 2006) and in the brown alga *Ectocarpus siliculosus* (Meslet-Cladière et al., 2013). The phloroglucinol synthase enzyme involved in phloroglucinol synthesis has been identified in these two species. They are the only two phloroglucinol synthases identified and characterized to date.

In *Pseudomonas fluorescens*, the phloroglucinol synthase is encoded by the PHLD gene (Achkar et al., 2005; Zha et al., 2006).

In *Ectocarpus siliculosus*, the phloroglucinol synthase is encoded by the PKS1 gene (Meslet-Cladière et al., 2013).

It has been possible to demonstrate PHLD phloroglucinol synthase activity in *Escherichia coli* expressing a heterologous PHLD gene (Achkar et al., 2005). This activity has been confirmed in vitro, by means of small-scale enzymatic tests carried out with a heterologous PHLD expressed and purified from recombinant *Escherichia coli* cultures (Zha et al., 2006).

PKS1 phloroglucinol synthase activity has been demonstrated in vitro, from recombinant PKS1 expressed and purified in *Escherichia coli* and from cell extracts of *E. siliculosus* (Meslet-Cladière et al., 2013, WO 2013/045510).

However, the PHLD and PKS1 enzymes exhibit low enzymatic activities. In addition, the possibility of synthesizing phloroglucinol in vitro on a large scale using these enzymes has never been proved. Finally, the phloroglucinol synthases used in these studies were produced by *E. coli* or *P. fluorescens* bacteria. The activity of these enzymes when they are produced by eukaryotics, such as yeasts or insect or mammalian cells, is thus unknown. However, the eukaryotic systems may be advantageous, in particular for large-scale productions. They in fact make it possible to obtain enzymes closer to the eukaryotic enzymes of origin, in particular because said enzymes can be modified at the post-translational level.

Thus, there is still the need to identify new phloroglucinol synthases which have a high phloroglucinol synthesis enzymatic activity in vitro or in vivo, which are suitable for industrial-scale production and which can be produced by eukaryotic systems.

The exact functional characterization of a polyketide synthase is, however, complicated by the fact that this class of enzymes brings together proteins which have large sequence similarities, whereas they can catalyse substantially dissimilar reactions and recognize entirely different substrates.

As a result, attempts to identify new phloroglucinol synthases in other organisms have not been successful. In particular, various strains of *Sargassum* sp. are known to be capable of producing phloroglucinol. In order to identify the enzymes responsible for the synthesis of this product, putative type III polyketide synthases were identified in *S. binderi*. These candidate enzymes were tested for phloroglucinol synthase activity. These tests revealed that none of these type III polyketide synthases identified in *S. binderi* exhibited this activity (Baharum et al., 2011).

Despite these difficulties, the present inventors have been able to identify polypeptides which have phloroglucinol synthase activity. Thus, new phloroglucinol synthases have been identified in ochrophyte algae, in particular in *S. binderi* and *A. anophagefferens*. They constitute the first example of phloroglucinol synthases in algae of this type. The inventors demonstrate here that these new phloroglucinol synthases exhibit a high phloroglucinol synthesis activity. They are thus suitable for industrial-scale production. Furthermore, they are functional when they are produced in a eukaryotic system.

SUMMARY OF THE INVENTION

In the context of the present invention, the inventors have demonstrated, entirely surprisingly, that living organisms, in addition to P. fluorescens and E. siliculosus, contain in their genome a gene encoding a type III polyketide synthase having a functional phloroglucinol synthase activity.

The present invention thus relates to polypeptides chosen from type III polyketide synthases, in particular type III polyketide synthases of eukaryotic ochrophyte algae, and also to the use thereof as phloroglucinol synthases.

The present invention also relates to isolated nucleic acid molecules encoding phloroglucinol synthases, in particular encoding phloroglucinol synthases of eukaryotic ochrophyte algae, and also to the phloroglucinol synthases thus encoded.

The invention also relates to vectors comprising at least one isolated nucleic acid molecule encoding such a phloroglucinol synthase.

The invention also relates to host cells comprising at least one isolated nucleic acid molecule or at least one vector according to the invention.

The invention also relates to methods for producing a functional phloroglucinol synthase.

The invention also relates to methods for producing phloroglucinol.

DESCRIPTION OF THE FIGURES

FIG. 1 shows the protein sequence alignments of the enzymes or candidates of algae PKS1.Es (PHLD.Es), PHLD.Sbi and PHLD-1.Aa and also that of the *Pseudomonas fluorescens* bacterium PHLD.Pf, formed with the Clustal W software.

FIG. 4 shows the localization of the genomic sequence of *A. anophageferens* encoding a peptide sequence homologous to the amino-terminal portion of PHLD.Sbi (sequence highlighted in light grey, framed by 2 black arrows) located 5' of the sequence of the PHLD.Aa gene (dark grey arrow) as annotated in the genomic databanks.

(C) Level of phloroglucinol production (in mg.l$^{-1}$) measured in the culture medium. (D) Level of phloroglucinol production (in mg.l$^{-1}$) standardized relative to the number of copies integrated into the genome.

Figure 9:
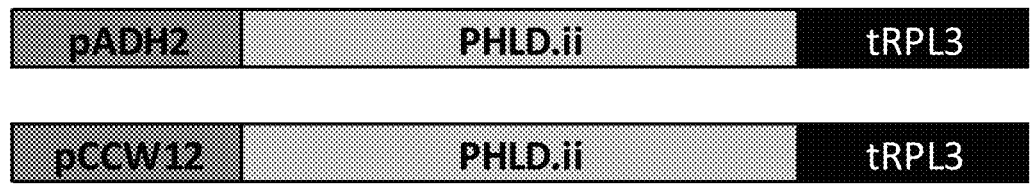

FIG. 9 shows the structure of the gene constructs integrated into the genome of the yeast at the JLP1 locus. The gene encoding each PHLD/PKS1 is under the control of the pADH2 promoter or of the pCCW12 promoter.

FIG. 10 shows the levels of phloroglucinol production in the yeast strains expressing the various PHLD.ii genes (only 1 copy) under the control of the ADH2 promoter after 48 hours of culture in a 24-well plate in the presence of 20 g.l$^{-1}$ of ethanol as carbon source at 30° C. (A) Summary of the various data measured. (B) Optical densities (OD) of the various cultures measured at 600 nm (OD$_{600}$), indicating the level of growth of each strain. (C) Level of phloroglucinol production (in mg.l$^{-1}$) measured in the culture medium.

FIG. 11 shows the levels of phloroglucinol production in the yeast strains expressing the various PHLD.ii genes (only 1 copy) under the control of the CCW12 promoter after 48 hours of culture in a 24-well plate in the presence of 20 g.l$^{-1}$ of glucose as carbon source at 30° C. (A) Summary of the various data measured. (B) Optical densities (OD) of the various cultures measured at 600 nm (OD$_{600}$), indicating the level of growth of each strain. (C) Level of phloroglucinol production (in mg.l$^{-1}$) measured in the culture medium.

DETAILED DESCRIPTION OF THE INVENTION

Definitions

The term "type III polyketide synthase" is intended to mean a multifunctional enzyme or an enzymatic complex producing polyketides and which does not use an acyl carrier protein (or ACP) domain.

The term "polyketide" is intended to mean a large family of secondary metabolites in bacteria, mycetes, plants and certain animal lines which originate from the iterative condensation of acetyl or malonyl subunits by polyketide synthase enzymes. Polyketides also serve as starting materials for the production of a wide range of natural and semi-synthetic products.

The term "phloroglucinol" is intended to mean an aromatic organic compound benzene-1,3,5-triol having the following chemical formula (formula I):

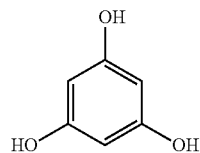

Formula I

The term "phloroglucinol synthase" is intended to mean a multifunctional enzyme or an enzymatic complex which belongs to the family of type III polyketide synthases and which catalyses phloroglucinol synthesis. A phloroglucinol synthase catalyses the condensation of three malonyl-CoA molecules so as to form a phloroglucinol molecule.

The term "enzymatic activity" or "catalytic activity" or else "activity" of an enzyme is intended to mean the efficiency of an enzyme to convert a substrate into a product in a given environment. The efficiency of the enzyme takes into account here the rate of conversion of the substrate into a product by the enzyme and the degree of conversion of the substrate into a product by the enzyme. The expression "degree of conversion of the substrate into a product by the enzyme" is intended to mean here the ratio between the amount of final product obtained relative to the initial amount of substrate for a defined amount of enzyme. For example, for the purposes of the invention, an enzymatic activity can be expressed as an amount of phloroglucinol produced in a given volume (for example in g.l$^{-1}$ or mg.l$^{-1}$).

The term "alga" is intended to mean an organism capable of oxygenic photosynthesis and the lifecycle of which generally takes place in an aquatic medium. Algae comprise the cyanobacteria and the eukaryotic algae. The term "cyanobacterium" is intended to mean a prokaryotic organism belonging to the group of *Cyanobacteria*, also known as blue algae. The term "eukaryotic alga" is intended to mean a eukaryotic organism belonging to the group of eukaryotic algae, comprising the branches of *Glaucophyta* or *Glauco-* cystophyta, Rhodophyta, Chlorobionta or Viridiplantae, Cryptophyta, Euglenozoa, Cercozoa, Haptophyta or Prymnesiophyta, Dinophyta, and Ochrophyta or Heterokontophyta.

The term "ochrophyte alga" or "ochrophyte" is intended to mean an alga belonging to the branch of Ochrophyta also known as Heterokontophyta, ochrophytes or heterocontophytes. The ochrophyte algae are golden-brown-coloured eukaryotic algae of the kingdom Chromista.

The term "Marista alga" or "Marista" is intended to mean an ochrophyte alga belonging to the Marista sub-branch. The Marista sub-branch comprises in particular the class Phaeophyceae and the class Pelagophyceae.

The term "brown alga" is intended to mean an organism belonging to the class of brown algae also known as Phaeophyceae and belonging to the branch of Ochrophyta. Brown algae use, as light-collecting pigment, chlorophyll c combined with a brown pigment, fucoxanthin. Their size varies from the microscopic scale to approximately ten metres long. Brown algae comprise in particular algae of the Ectocarpus and Sargassum genera.

The term "pelagophyte alga" or "pelagophyte" is intended to mean an organism belonging to the class of algae Pelagophyceae, also known as pelagophytes, and belonging to the branch of Ochrophyta. The pelagophytes form a small group of eukaryotic microalgae.

The term "Ectocarpus sp." is intended to mean an alga of the Ectocarpus genus, of the class of brown algae, belonging to the family Ectocarpaceae. The Ectocarpus genus comprises in particular the species Ectocarpus siliculosus.

The term "Sargassum sp." or "sargassum" is intended to mean an alga of the Sargassum genus, of the class of brown algae, belonging to the family Sargassaceae. The Sargassum genus comprises in particular the species Sargassum binderi (also known as Sbi hereinafter).

The term "Aureococcus sp." is intended to mean an alga of the Aureococcus genus, of the class of pelagophyte algae. The Aureococcus genus comprises in particular the species Aureococcus anophagefferens (also known as Aa hereinafter).

The term "Pseudomonas sp." is intended to mean a Gram-negative (Gram-) bacterium, which does not form spores (or non-sporulating), which is in the form of a bacillus and which is necessarily aerobic, of the Pseudomonas genus. The Pseudomonas genus comprises in particular the species Pseudomonas fluorescens (also known as Pf hereinafter).

The term "PHLD.Pf" is intended to mean, without distinction, the gene encoding the PHLD phloroglucinol synthase of P. fluorescens, and also all the products of this gene, including the RNAs and the polypeptides encoded by this gene.

The term "PKS1.Es" or "PHLD.Es" is intended to mean, without distinction, the gene encoding the PKS1 phloroglucinol synthase of E. siliculosus, and also all the products of this gene, including the RNAs and the polypeptides encoded by this gene.

The term "PhlD" or "PHLD" denotes here a candidate gene encoding a candidate phloroglucinol synthase enzyme, and also all the products of this gene, including the RNAs and the polypeptides encoded by this gene. According to the nomenclature chosen by the inventors, the term "PhlD.ii" or "PHLD.ii" denotes here the candidate gene or the candidate polypeptide from a given organism. The letters "ii" represent the genus and the species to which said organism belongs.

The term "nucleic acid molecule" is intended to mean a polymer of any length of deoxyribonucleic acid (DNA), or polydeoxyribonucleotides, including in particular complementary DNAs or cDNAs, genomic DNAs, plasmids, vectors, viral genomes, isolated DNA, probes, primers and any mixture thereof; or a polymer of any length of ribonucleic acid (RNA), or polyribonucleotides, including in particular messenger RNAs or mRNAs, antisense RNAs; or mixed polyribo-polydeoxyribonucleotides. They encompass single-stranded or double-stranded, linear or circular, and natural or synthetic polynucleotides. In addition, a polynucleotide can comprise non-natural nucleotides and can be interrupted by non-nucleotide components.

In the context of the present invention, the terms "nucleic acid", "nucleic acid molecule", "polynucleotide" and "nucleotide sequence" are used interchangeably.

The term "isolated molecule" is intended to mean a molecule, in particular a protein, a polypeptide, a peptide, a nucleic acid molecule, a plasmid vector, a viral vector or a host cell, which is extracted from its natural environment (that is to say separated from at least one other component with which it is naturally associated).

The term "polypeptide", "protein" and "peptide" is intended to mean polymers of amino acid residues which comprise at least nine amino acids bonded via peptide bonds. The polymer may be linear, branched or cyclic. The polymer may comprise natural amino acids and/or amino acid analogues and it may be interrupted by non-amino acid residues. As a general indication and without however being bound thereto in the present application, if the amino acid polymer contains more than 50 amino acid residues, it is preferably referred to as a polypeptide or a protein, whereas if the polymer consists of 50 amino acids or less, it is preferably referred to as a "peptide".

The term "vector" is intended to mean a carrier, preferably a nucleic acid molecule or a viral particle, which contains the elements required to enable one or more nucleic acid molecule(s) to be administered into, propagated in and/or expressed in a host cell or an organism.

From a functional point of view, this term encompasses maintenance vectors (cloning vectors), vectors for expression in various host cells or organisms (expression vectors), extrachromosomal vectors (for example multicopy plasmids) or integrating vectors (for example designed to integrate into the genome of a host cell and to produce additional copies of the nucleic acid molecule that it contains when the host cell replicates). This term also encompasses shuttle vectors (for example, which function both in prokaryotic hosts and/or eukaryotic hosts) and transfer vectors (for example for the transfer of nucleic acid molecule(s) into the genome of a host cell).

From a structural point of view, the vectors according to the invention may be natural, synthetic or artificial genetic sources, or a combination of natural and artificial genetic elements.

Thus, in the context of the invention, the term "vector" should be understood broadly while including plasmid vectors (or plasmids) and viral vectors.

A "plasmid" as used here denotes a replicatable DNA construct. Usually, plasmid vectors contain selectable marker genes which allow the host cells carrying the plasmid to be identified and/or selected positively or negatively in the presence of the compound corresponding to the selectable marker. A variety of positive and negative selectable marker genes are known in the art. By way of illustration, an antibiotic resistance gene can be used as a positive selectable marker gene for selecting a host cell in the presence of the corresponding antibiotic.

The term "viral vector" as used here refers to a nucleic acid vector which comprises at least one element of a viral genome and which can be packaged in a viral particle, or a viral particle. The viral vectors may be replication-competent or selective (for example, designed to replicate better or selectively in specific host cells), or may be genetically deactivated so as to be defective or replication-deficient.

The term "host cell" is intended to mean a cell containing a nucleic acid molecule according to the invention. Advantageously again, the host cell is capable of expressing a polypeptide with phloroglucinol synthase activity and/or of producing the vector of the invention. Advantageously, the host cell is capable of synthesizing phloroglucinol.

The host cell may consist of a single type of cells or of a group of different types of cells. The host cell may also be a hybrid cell, that is to say a cell resulting from the fusion of at least two cells of different type.

The host cell may belong to cultured cell lines, to primary cells, to stem cells or to proliferative cells. In the context of the invention, the term "host cells" comprises prokaryotic cells, lower eukaryotic cells such as yeast cells, and other eukaryotic cells such as insect cells, plant cells and mammalian cells (for example human or nonhuman cells, preferably nonhuman cells).

The term "host cell" comprises more broadly cells which contain or have contained the nucleic acid molecule according to the invention, and also the progeny of such cells. The host cell may for example be isolated or organized in a tissue or in an organ or else may be within a complete organism. In the case where the host cell is within a complete organism, said organism is not human.

It is thus clear that a "host cell" according to the present invention is a recombinant host cell, i.e. a cell housing an exogenous genetic material. Thus, a host cell is not a wild-type cell that exists naturally, but is a molecular biology tool obtained by genetic manipulation techniques.

The term "identity" is intended to mean an exact sequence correspondence between two polypeptides or two amino acid molecules. The "percentage identity" between two sequences depends on the number of identical residues common to the two sequences, and takes into account the number of intervals that must be introduced for an optimal alignment and the length of each interval. Various computer programs and mathematical algorithms are available in the prior art for determining the percentage identity between amino acid sequences, such as for example the Blast program available on the NCBI or ALIGN base (Atlas of Protein Sequence and Structure, Dayhoff (ed.), 1981, Suppl. 3 482-489). Programs for determining the homology between nucleotide sequences are also available in a specialized database (for example Genbank, the Wisconsin Sequence Analysis Package, the BESTFIT, FASTA and GAP programs).

By way of illustration, the expression "at least 80% sequence identity", as used here, represents 80%, 81%, 82%, 83%, 84%, 85%, 86%, 87%, 88%, 89%, 90%, 91%, 92%, 93%, 94%, 95%, 96%, 97%, 98%, 99% or 100%.

In the detailed description which follows, the embodiments may be taken alone or combined appropriately by those skilled in the art.

Isolated Polypeptides and Use thereof as Phloroglucinol Synthases

The inventors have identified, entirely surprisingly, genes encoding new type III polyketide synthases in the genome of living organisms that were not known to encode this type of enzyme. The inventors have in particular demonstrated, for the first time, that these novel type III polyketide synthases have phloroglucinol synthase activity.

The present invention thus relates to isolated polypeptides chosen from type III polyketide synthases, in particular type III polyketide synthases of eukaryotic ochrophyte algae.

The present invention relates in particular to an isolated polypeptide with phloroglucinol synthase activity, comprising at least one amino acid sequence having at least 80% identity with the sequence SEQ ID No.: 3. Preferably, the isolated polypeptide with phloroglucinol synthase activity comprises at least one amino acid sequence having at least 85% identity, more preferably at least 90% identity, more preferably at least 91% identity, more preferably at least 92% identity, more preferably at least 93% identity, more preferably at least 94% identity, still more preferably at least 95% identity, still more preferably at least 96% identity, still more preferably at least 97% identity, still more preferably at least 98% identity, and even more preferentially at least 99% identity with the sequence SEQ ID No.: 3.

According to one embodiment, the isolated polypeptide with phloroglucinol synthase activity comprises at least one amino acid sequence of sequence SEQ ID No.: 3.

In one preferred embodiment, the isolated polypeptide with phloroglucinol synthase activity has the amino acid sequence of sequence SEQ ID No.: 3, the sequence of which is indicated in Table 2 below.

Advantageously, the isolated polypeptide with phloroglucinol synthase activity is the isolated PHLD polypeptide of *Aureococcus anophagefferens*, in particular PHLD-1.Aa, of SEQ ID No.: 3. Indeed, the inventors have identified, entirely surprisingly, a new protein, PHLD-1.Aa, which was not described in the various databases available to those skilled in the art. The inventors have shown that this new PHLD-1.Aa protein is a type III polyketide synthase and that it has a phloroglucinol synthase activity.

According to one embodiment, the polypeptide with phloroglucinol synthase activity is isolated from strains of *Aureococcus anophagefferens* in culture.

According to one embodiment, the polypeptide with phloroglucinol synthase activity is isolated from a heterologous host cell expressing said polypeptide, said host cell being as defined above and as described below in the section "host cells".

According to one embodiment, the isolated polypeptide with phloroglucinol synthase activity is synthesized in vitro by means of protein synthesis techniques that those skilled in the art know perfectly well how to define.

According to one embodiment, the isolated polypeptide with phloroglucinol synthase activity is recombinant.

The present invention also relates to the use of isolated polypeptides chosen from the type III polyketide synthases, as phloroglucinol synthases, preferably with the exclusion of the type III polyketide synthase PHLD of *Pseudomonas fluorescens* and of the type III polyketide synthases of *Ectocarpus siliculosus* chosen from pKS1.Es, pKS2.Es and pKS3.Es, more preferably with the exclusion of pKS1.Es.

According to one embodiment, said polypeptide is chosen from the type III polyketide synthases of algae, preferably of eukaryotic algae.

The present invention relates in particular to the use of at least one polypeptide chosen from the type III polyketide synthases of algae, as phloroglucinol synthase, with the exclusion of the type III polyketide synthases of *Ectocarpus siliculosus* chosen from PKS1.Es, PKS2.Es and PKS3.Es.

In one preferred embodiment, said polypeptide is chosen from the type III polyketide synthases of ochrophyte algae, preferably of *Marista* algae, more preferably of algae belonging to the class of brown algae or to the class of pelagophyte algae.

Advantageously, said polypeptide comprises at least one amino acid sequence having at least 80% identity with a sequence chosen from SEQ ID No.: 1 and SEQ ID No.: 3, the sequences of which are indicated in Table 2 below.

According to one embodiment, said isolated polypeptide is chosen from the type III polyketide synthases of brown algae, preferably with the exclusion of the type III polyketide synthases of *Ectocarpus siliculosus* chosen from PKS1.Es, PKS2.Es and PKS3.Es, preferably with the exclusion of PKS1.Es. Advantageously, said isolated polypeptide is chosen from the type III polyketide synthases of Sargassum sp. algae, in particular *Sargassum binderi* algae.

According to another advantageous embodiment, said polypeptide is chosen from the type III polyketide synthases of pelagophyte algae. Advantageously, said isolated polypeptide is chosen from the type III polyketide synthases of *Aureococcus* sp. algae, in particular *Aureococcus anophageff6rens* algae.

According to one embodiment, said polypeptide comprises at least one amino acid sequence preferably having at least 80% identity, more preferably at least 85% identity, more preferably at least 90% identity, even more preferably at least 91% identity, still more preferably at least 92% identity, even more preferentially at least 93% identity, even more preferentially at least 94% identity, more preferably at least 95% identity, more preferably at least 96% identity, even more preferably at least 97% identity, still more preferably at least 98% identity, and even more preferentially at least 99% identity, with a sequence chosen from SEQ ID No.: 1 and SEQ ID No.: 3.

According to one particularly advantageous embodiment, said polypeptide comprises at least one amino acid sequence chosen from SEQ ID No.: 1 and SEQ ID No.: 3.

In one preferred embodiment, the isolated polypeptide with phloroglucinol synthase activity has an amino acid sequence chosen from SEQ ID No.: 1 and SEQ ID No.: 3.

Advantageously, the isolated polypeptide with phloroglucinol synthase activity is chosen from the isolated polypeptide with phloroglucinol synthase activity PHLD.Sbi of *Sargassum binderi* and the isolated polypeptide with phloroglucinol synthase activity PHLD-1.Aa of *Aureococcus anophageffgerens*.

Isolated Nucleic Acid Molecules

The present invention relates to isolated nucleic acid molecules encoding at least one polypeptide chosen from type III polyketide synthases, in particular type III polyketide synthases of eukaryotic ochrophyte algae.

Advantageously, said polypeptide is as defined above.

According to one embodiment, the isolated nucleic acid molecule comprises a promoter controlling the expression of at least one nucleic acid sequence encoding a polypeptide as defined above. Thus, according to one embodiment, the present invention relates to an isolated nucleic acid molecule comprising at least one nucleic acid sequence encoding a polypeptide chosen from the type III polyketide synthases as defined above and also comprising a promoter controlling the expression of said at least one nucleic acid sequence.

Advantageously, the promoter is an exogenous promoter, in particular a yeast promoter, preferably a promoter chosen from ADH2 (pADH2) and CCW12 (pCCW12), more preferably a promoter chosen from ADH2 (pADH2) of *Saccharomyces cerevisiae* and CCW12 of *S. cerevisiae*, more preferably a promoter chosen from ADH2 (pADH2) of SEQ ID No.: 7 and CCW12 of SEQ ID No.: 8.

According to one embodiment, the isolated nucleic acid molecule comprises a transcription terminator for at least one nucleic acid sequence encoding a polypeptide as defined above. Thus, according to one embodiment, the present invention relates to an isolated nucleic acid molecule comprising at least one nucleic acid sequence encoding a polypeptide chosen from the type III polyketide synthases as defined above and also comprising a terminator controlling the expression of said at least one nucleic acid sequence.

Advantageously, the terminator is an exogenous terminator, in particular a yeast terminator, preferably the RPL3 terminator (tRPL3), more preferably the RPL3 terminator of *S. cerevisiae*, more preferably the RPL3 terminator of SEQ ID No.: 9.

According to one preferred embodiment, the isolated nucleic acid molecule comprises both a promoter and a terminator which are as defined above. Thus, according to one embodiment, the present invention relates to an isolated nucleic acid molecule comprising at least one nucleic acid sequence encoding a polypeptide chosen from the type III polyketide synthases as defined above and also comprising a promoter and a terminator controlling the expression of said at least one nucleic acid sequence.

According to one embodiment, the nucleic acid molecule also comprises an export sequence. Advantageously, this export sequence allows the secretion or excretion of the polypeptide(s) encoded by said nucleic acid molecule, in the cell medium.

According to one embodiment, the nucleic acid molecule is isolated from homologous strains in culture, preferably chosen from *Sargassum binderi* and *Aureococcus anophageffgerens*.

According to one embodiment, the nucleic acid molecule is isolated from a heterologous vector or host cell comprising said molecule, said vector or said host cell being as defined below in the section "Vectors" or "Host cells".

According to one embodiment, the isolated nucleic acid molecule is synthesized in vitro by means of nucleic synthesis techniques that those skilled in the art know perfectly well how to define.

According to one embodiment, the isolated nucleic acid molecule is recombinant.

Isolated Nucleic Acid Molecules of Sequence PHLD-1.Aa

According to another aspect, the present invention relates to isolated nucleic acid molecules comprising the sequence PHLD-1.Aa.

In accordance with the above definitions, the term "PHLD-1.Aa" is intended to mean, without distinction, the gene encoding the phloroglucinol synthase PHLD-1.Aa of *Aureococcus anophageffgerens*, and also all the products of this gene, including the RNAs and the polypeptides encoded by this gene.

According to one embodiment, the isolated nucleic acid molecule comprising the PHLD-1.Aa sequence comprises at least one nucleic acid sequence comprising at least 80% identity with the sequence SEQ ID No.: 4. Preferably, said isolated nucleic acid molecule comprises at least one nucleic acid sequence having at least 85% identity, more preferably at least 90% identity, more preferably at least 91% identity, more preferably at least 92% identity, more preferably at least 93% identity, even more preferably at least 94% identity, still more preferably at least 95% identity, still more preferably at least 96% identity, still more preferably at least 97% identity, still more preferably at least 98% identity, and even more preferentially at least 99% identity with the sequence SEQ ID No.: 4.

According to one embodiment, the isolated nucleic acid molecule comprising the PHLD-1.Aa sequence comprises at least one amino acid sequence of sequence SEQ ID No.: 4.

In one preferred embodiment, said isolated nucleic acid molecule has the sequence PHLD-1.Aa. Preferably, said PHLD-1.Aa sequence is the sequence SEQ ID No.: 4, the sequence of which is indicated in Table 2 below.

According to one embodiment, said isolated nucleic acid molecule is isolated from strains of Aureococcus anophageferens in culture.

According to one embodiment, said isolated nucleic acid molecule is isolated from a heterologous vector or host cell comprising said molecule, said vector or said host cell being as defined below in the section "Vectors" or "Host cells".

According to one embodiment, said isolated nucleic acid molecule is synthesized in vitro by means of nucleic synthesis techniques that those skilled in the art know perfectly well how to define.

According to one embodiment, said isolated nucleic acid molecule is recombinant.

According to various embodiments, said isolated nucleic acid molecule is in accordance with the description above in the section "Isolated nucleic acid molecules".

In particular, said isolated nucleic acid molecule may comprise a transcription promoter and/or terminator and/or an export sequence (see above for further details).

Vectors

The present invention relates to vectors comprising at least one nucleic acid molecule as defined above.

The vectors that are suitable in the context of the present invention comprise, without limitation, bacteriophage, plasmid or cosmid vectors for expression in prokaryotic host cells such as bacteria (for example *E. coli*, or bacteria of the *Pseudomonas* genus); vectors for expression in yeast (for example *Saccharomyces cerevisiae, Schyzosaccharomyces pombe, Pichia pastoris*); baculovirus vectors for expression in insect cell systems (for example, Sf9 cells); viral and plasmid vectors for expression in plant cell systems (for example, the Ti plasmid, the cauliflower mosaic virus CaMV, the tobacco mosaic virus TMV); and also viral and plasmid vectors for expression in higher eukaryotic cells or organisms.

These vectors are generally commercially available (for example, from suppliers such as Invitrogen, Stratagene, Amersham Biosciences, Promega, etc.), available from deposit institutions such as the American Type Culture Collection (ATCC, Rockville, Md.), or have been the subject of numerous publications describing their sequence, their structure and the methods for producing them, so that those skilled in the art can apply them without difficulty.

Representative examples of suitable plasmid vectors comprise, without limitation, pREP4, pCEP4 (Invitrogen), pCI (Promega), pVAX (Invitrogen) and pgWiz (Gene Therapy System Inc).

Thus, advantageously, the vector is a plasmid.

Host Cells

In another aspect, the present invention relates to host cells comprising at least one nucleic acid molecule or at least one vector as defined above.

According to various embodiments, said host cell, in particular said heterologous host cell mentioned above, can be a prokaryotic cell, a lower eukaryotic cell such as a yeast cell, and other eukaryotic cells such as insect cells, plant cells and mammalian cells (for example human or nonhuman cells, preferably nonhuman cells).

Advantageously, the host cell is a microorganism selected from bacteria, yeasts, fungi, algae and cyanobacteria.

The host cell is preferably a yeast, said yeast being in particular selected from the *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia* genera.

Even more particularly, the yeast is selected from the species *Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata*.

Even more particularly, the yeast is of the *Saccharomyces* genus, preferably of the species *Saccharomyces cerevisiae*.

According to one embodiment, the host cell comprises at least one copy of the nucleic acid molecule as defined above, integrated into its genome.

According to one embodiment, the host cell comprises a single copy of the nucleic acid molecule as defined above, integrated into its genome.

When the host cell is a yeast cell, the copy or copies of the nucleic acid molecule can be integrated at various loci, preferentially at the URA3 locus, at the JLP1 locus, at the LEU2 locus, or at the TRP1 locus of the genome of said yeast cell. When the host cell is a yeast cell and several copies of the nucleic acid molecule are integrated, the various copies can be integrated at the same locus, or else at different loci, preferentially at any one of the combinations of the URA3, JLP1, LEU2 and/or TRP1 loci.

Advantageously, the codons used in the nucleic acid molecule have been adapted for optimal expression in the host cell selected.

An optimal expression can in particular be obtained when the codons chosen are those preferentially used by the organism of origin of the host cell. The preferentially used codons are known for most organisms commonly used in the field. Those skilled in the art will be able to easily determine the most advantageous codons to be used as a function of the host cell chosen.

To this effect, those skilled in the art know which technique to use in order to modify the codons of the nucleic acid molecule. The codons can for example be modified by in vitro site-directed mutagenesis using a sample of the nucleic acid molecule of which the codons are to be adapted, by means of an amplification by polymerase chain reaction (PCR). Alternatively, the nucleic acid molecule can be synthesized in vitro directly with the optimized codons.

The host cells can be cultured in small-scale and large-scale, aerobic or anaerobic bioreactors, in flasks or in Petri dishes. The culture can be performed at a temperature, at a pH, in a culture medium and at an oxygen content that are suitable for a given host cell.

Methods

Method for Producing a Polypeptide with Phloroglucinol Synthase Activity

The present invention also relates to a method for producing a polypeptide with phloroglucinol synthase activity as defined above.

According to one embodiment, the method for producing a polypeptide with phloroglucinol synthase activity as defined above comprises at least the steps consisting in:
(i) introducing a nucleic acid molecule or a vector as described above into a suitable host cell in accordance with the preceding description; and (ii) culturing, in vitro, said host cell obtained in step (i) under conditions which allow the growth of said host cell and/or the expression of said nucleic acid molecule, so as to produce said polypeptide.

According to another embodiment, the method for producing a polypeptide with phloroglucinol synthase activity as defined above comprises at least the step consisting in:
(i) culturing, in vitro, a host cell expressing said polypeptide, for example a host cell as described above, under conditions which allow the growth of said host cell and/or the expression of the nucleic acid molecule contained in said host cell, so as to produce said polypeptide.

Advantageously, the method for producing a polypeptide with phloroglucinol synthase activity comprises at least one additional step chosen from the steps consisting in:
(a) recovering the cells expressing said polypeptide, obtained after the culturing step; and
(B) purifying the polypeptide from the cells recovered in step (a).

Method for Producing Phloroglucinol

The present invention also relates to a method for producing phloroglucinol.

According to one embodiment M1, the method for producing phloroglucinol comprises at least the steps consisting in:
(i) obtaining cells by implementing one of the methods described above;
(ii) bringing the cells obtained in step (i) into contact with a suitable substrate;
(iii) incubating the mixture resulting from step (ii) under conditions suitable for producing phloroglucinol;
(iv) optionally, recovering the reaction medium comprising the phloroglucinol, obtained after step (iii); and
(v) optionally, purifying the phloroglucinol from the reaction medium of step (iv).

According to another embodiment M2, the method for producing phloroglucinol comprises the steps consisting in:
(i) bringing a host cell expressing the polypeptide with phloroglucinol synthase activity as defined above, for example a host cell as defined above, into contact with a suitable substrate;
(ii) culturing, in vitro, the host cell of step (i) under conditions which allow the growth of said host cell and/or the expression of the nucleic acid molecule contained in said host cell, so as to produce phloroglucinol;
(iii) optionally, recovering the culture medium comprising the phloroglucinol, obtained after step (ii); and
(iv) optionally, purifying the phloroglucinol from the culture medium of step (iii).

For the purposes of methods M1 and M2, the substrate is a carbon source. Advantageously, the carbon source is a pure carbon source or an industrial coproduct (such as molasses or green syrup, for example from the sugar industry). Preferably, the substrate in the pure carbon source or the industrial coproduct is a simple sugar, such as glucose (or dextrose), fructose, galactose, mannose, sucrose, lactose or maltose; a complex sugar, such as a monosaccharide, a disaccharide or trisaccharides, or else a polysaccharide such as starch; an alcohol, such as ethanol; an acid; a fatty acid and the ester derivative thereof; or a mixture of sugars, of alcohols, of acids and/or of fatty acids or the ester derivatives thereof.

Preferably, the substrate is glucose or sucrose. Alternatively, the substrate is ethanol.

According to another embodiment M3, the method for producing phloroglucinol comprises at least the steps consisting in:
(i) bringing at least one polypeptide obtained in step (B) of the method as described above into contact with a suitable substrate;
(ii) incubating the mixture resulting from step (i) under conditions suitable for producing phloroglucinol;
(iii) optionally, recovering the reaction medium comprising the phloroglucinol, obtained after step (ii); and
(iv) optionally, purifying the phloroglucinol from the reaction medium of step (iii).

According to another embodiment M4, the method for producing phloroglucinol comprises at least the steps consisting in:
(i) bringing at least one polypeptide as defined above into contact with a suitable substrate;
(ii) incubating the mixture resulting from step (i) under suitable conditions for producing phloroglucinol;
(iii) optionally, recovering the reaction medium comprising the phloroglucinol, obtained after step (ii); and
(iv) optionally, purifying the phloroglucinol from the reaction medium of step (iii).

For the purposes of the methods M3 and M4, the substrate is a thioester. Advantageously, the substrate is an acyl-Coenzyme A (or acyl-CoA) such as malonyl-CoA, acetyl-CoA, hexanoyl-CoA, decanoyl-CoA, lauroyl-CoA and palmitoyl-CoA, or a mixture thereof. Preferably, the substrate is malonyl-CoA.

According to one preferred embodiment, the purification of the phloroglucinol is carried out by liquid-liquid extraction.

The examples which follow aim to illustrate the present invention without any limitation.

The enzymes respectively encoded by the PHLD gene of *Pseudomonas fluorescens* (Zha et al., 2006), and by the PKS1 gene of *Ectocarpus siliculosus* (Meslet-Cladière et al., 2013) are used therein as controls.

EXAMPLES

Example 1

Identification of New Candidate Phloroglucinol Synthases

Up until the present invention, only two phloroglucinol synthases had been identified and characterized:
the enzyme encoded by the PHLD gene of *Pseudomonas fluorescens* (Zha et al., 2006), and
the enzyme encoded by the PKS1 gene of *Ectocarpus siliculosus* (Meslet-Cladière et al., 2013).

The inventors have now discovered and characterized new phloroglucinol synthases using genetic and functional analyses.

As indicated in the introduction above, the exact functional characterization of a polyketide synthase is complex since this class of enzymes groups together proteins having high sequence similarities although they can catalyse substantially dissimilar reactions and recognize entirely different substrates.

1.1. Selection of New Candidate Enzymes

In order to identify new phloroglucinol synthases, the inventors identified sequences encoding putative type III polyketide synthases. The sequences of these putative type III polyketide synthases thus identified by the inventors were analysed and aligned with respect to one another using in particular as a basis the type III polyketide synthase alignment published by Meslet-Cladière et al. 2013.

The analysis of this sequence alignment resulted in the selection of a group of candidate enzymes, the protein sequences of which are close to that of the product of the PKS1.Es gene of the alga *Ectocarpus siliculosus* (Tables 1 and 2):

TABLE 1

Putative type III polyketide synthases identified. The shaded rows show the enzymes which have a known phloroglucinol synthase activity.

| Name | Reference in the databases | Known or putative function | Species | Kingdom |
|---|---|---|---|---|
| PHLD.Pf | AAY95147.1 | PHLD type III polyketide synthase | *Pseudomonas fluorescens* Pf-5 | Gammaproteobacteria/ pseudomonals (bacteria) |
| PKS1.Es | CBN7619.1 | Type III polyketide synthase without signal peptide 2-32 | *Ectocarpus siliculosus* | Ochrophytes (algae) |
| PHLD.Sbi | ADK13089.1 | Putative type III polyketide synthase | *Sargassum binderi* | Ochrophytes (algae) |
| PHLD.Aa | XP_009036155.1 | Putative protein | *Aureococcus anophagefferens* | Ochrophytes (algae) |
| PHLD-1.Aa | Not described | n. a. | *Aureococcus anophagefferens* | Ochrophytes (algae) |

TABLE 2

Protein or nucleic sequences of the putative type III polyketide synthases identified

| SEQ ID No.: | Name | Protein or nucleic sequence |
|---|---|---|
| SEQ ID No.: 1 | PHLD.Sbi | MSSAAVAMLADPTVQIALACIVLSLIVVF RSYRKGKDEQTVYPVIAGMAIGNPQYRCT QDQALTVAQKCPGVESVKPVLERIYGNSR IGSRYFAVPDFTPNQAAKGDPMFFPADGS FEVPVDTRLDKFKEKAVPLVSDVARRAIK EAGIDVSDVSKLVVVSSTGFLGPGLDCEL IKNLGLTRSVDRTLIGFMGCAAAMNGFRN ANDFVTANPGKYALMICVELSSVHTTFDD NINDAILHAIFADGCAAAVLKGVRKEAPK GTLAIVDNHAWLMEGTEDGITLAIKPNGI TCTLSKFLPQYIAKNIAFFADGFLKKHNL GRDDVDFWCVHPGGRRIIEEAQNGLGLTE AQTADSWAVLAEYGNMLSPSVMFVLSRVF KRHNAALAQGKPGYQTGMAFSFSPGVGAE GILLRQI |
| SEQ ID No.: 2 | PHLD.Aa | MPVEKRLDMFREKSVPLVTKVCKDAMADA GIDVEQIGKLVVVSSTGFLGPGLDAELIK TLGLWRGVDRSLIGFMCAAAMNGFRVAN DFAMSHPGKMALMVCVEISSVHTTFDDNV NDAILHAIFADGCAAAVISGEKPGSAAAK GKFGIVDTHGWLMEGTEDGITLSINENGI SCILSKYLPQYIAKNMAGYVDSFLGMHGL QKTDMDFWAIHPGGRRIIEEAQNGLGLSE EQAKYSWTVLSQYGNMLSPSVMFVLELIL NDHKKALAKGERGLKQGIAFSFSPGVGAE GILINVM |
| SEQ ID No.: 3 | PHLD-1.Aa | mskkdekiipvimgmatgnppyrasqqqa laiaescpecnsikpvlariygnsridyr fmavpdftpeqklegdenffdkdlmfkMP VEKRLDMFREKSVPLVTKVCKDAMADAGI DVEQIGKLVVVSSTGFLGPGLDAELIKTL GLWRGVDRSLIGFMGCAAAMNGFRVANDF AMSHPGKMALMVCVEISSVHTTFDDNVND AILHAIFADGCAAAVISGEKPGSAAAKGK FGIVDTHGWLMEGTEDGITLSINENGISC ILSKYLPQYIAKNMAGYVDSFLGMHGLQK TDMDFWAIHPGGRRIIEEAQNGLGLSEEQ AKYSWTVLSQYGNMLSPSVMFVLELILND HKKALAKGERGLKQGIAFSFSPGVGAEGI LINVM |
| SEQ ID No.: 4 | PHLD-1.Aa | ATGTCGAAGAAGGATGAGAAGATCATCCC TGTCATCATGGGTATGGCCACAGGTAATC CGCCATACAGGGCGAGTCAACAACAAGCT CTAGCAATTGCGGAGTCCTGCCCAGAATG TAATAGCATTAAACCGGTATTGGCAAGAA TTTATGGTAATAGCCTATCGACTACAGG TTTATGGCAGTACCGGATTTCACACCCGA ACAGAAGCTTGAAGGTGACGAAAACTTCT TTGATAAAGATTTAATGTTTAAGATGCCA GTGGAGAAGAGATTGGACATGTTTAGGGA GAAGAGTGTGCCATTAGTCACGAAGGTCT GTAAGGATGCCATGGCAGACGCTGGTATA GACGTTGAACAGATTGGCAAACTTGTCGT GGTATCATCAACTGGCTTCTTAGGCCCTG GACTAGATGCGGAGTTAATTAAGACACTT GGACTTTGGCGTGGTGTTGACCGGTCTCT GATTGGATTCATGGGTTGTGCGGCGGCCA TGAACGGTTTTCGGGTTGCTAATGATTTC GCCATGTCCCACCCGGGAAAGATGGCCCT AATGGTTTGCGTCGAAATATCCTCTGTGC ATACCACATTCGATGATAACGTAAATGAT GCAATACTTCATGCGATCTTCGCCGATGG ATGTGCAGCCGCAGTAATATCGGGAGAGA AGCCAGGTTCTGCGGCGACGCAAAGGCAAA TTCGGAATCGTCGATACGCATGGTTGGCT CATGGAAGGCACAGAAGATGGGATAACCC TGTCTATCAATGAAATGGTATATCATGC ATCTTGAGTAAGTATCTACCACAGTATAT TGCAAAGAACATGGCAGGTTACGTAGATA GTTTCCTAGGGATGCATGGATTACAGAAG ACAGATATGGATTTCTGGGCTATTCACCC CGGCGGCCGCAGAATTATAGAGGAAGCGC AGAACGGTTTGGGTTTATCCGAGGAGCAG GCGAAGTATTCTTGGACTGTTCTTAGTCA GTATGGTAATATGTTGTCACCTAGCGTGA TGTTTGTGTTAGAACTGATCCTTAATGAC CACAAGAAGGCACTGGCAAAGGGAGAGCG CGGTTTAAAGCAAGGTATCGCATTTAGCT TCTCACCGGGTGTTGGGGCCGAGGGCATC CTCATTAATGTTATGTAA |

FIG. 1 presents the alignment of the protein sequences of the enzymes or candidates in the algae PKS1.Es, PHLD.Sbi and PHLD-1.Aa and also that of the *Pseudomonas fluorescens* bacterium PHLD.Pf. The alignment of the two candidate enzymes selected and of PKS1.Es with the PHLD.Pf enzyme was carried out using the Clustal W software.

Table 3 presents the matrix of the sequence identities that exist between these various enzymes.

TABLE 3

Matrix of the sequence identities that exist between the various candidate enzymes:

|          | PHLD.Pf | PHLD.Es | PHLD.Sbi | PHLD-1.Aa | PHLD.Cmi |
|----------|---------|---------|----------|-----------|----------|
| PHLD.Pf  | ID      | 23.1    | 21.5     | 21.5      | 21.5     |
| PHLD.Es  | 23.1    | ID      | 86.2     | 65.9      | 40.1     |
| PHLD.Sbi | 21.5    | 86.2    | ID       | 61.2      | 36.7     |
| PHLD-1.Aa| 21.5    | 65.9    | 61.2     | ID        | 38.5     |

The results show that the phylogenetic distance that exists between the enzyme of the PKS1.ES alga and the bacterial enzyme PHLD.Pf is considerable since less than 25% identity is observed between these two enzymes. It is not therefore possible to assign, a priori, a phloroglucinol synthase function to the putative polyketide synthases studied because of this strong sequence divergence.

1.2. Measurement of the Phloroglucinol Synthase Activities In Yeast

In order to identify the phloroglucinol synthases among the candidates identified above, a method of extracting and assaying phloroglucinol was developed as detailed below.

1.2.1. Phloroglucinol Extraction Method

The method was developed using resorcinol as internal standard. Various tests resulted in the development of a liquid-liquid extraction method carried out at pH 4.0 in the presence of ethyl acetate as solvent, and by saturating the aqueous phase with NaCl. The extraction is carried out for 30 min with circular shaking. The organic phase is removed and the ethyl acetate solvent is evaporated off under a stream of nitrogen $N_2$ at 30° C. The dry extract obtained after complete evaporation is then taken up in a predetermined volume of a 50%-50% ethanol/$H_2O$ mixture.

The extraction yield was measured by mass spectrometry after high pressure chromatography on a C18 column (dimensions: 100 mm×2.1 mm; particle size: 1.7 μm) using a 0.03% methanoic acid (HCOOH)/acetonitrile (ACN) gradient.

The extraction yields were determined and measured using solutions of phloroglucinol and resorcinol prepared in the culture medium used for the growth of the yeasts. The phloroglucinol concentrations correspond to the bottom (20 μg·ml$^{-1}$) and top (200 μg·ml$^{-1}$) points of the assay range. The resorcinol concentration corresponds to the concentration added as internal standard during the assays (200 μg·ml$^{-1}$). The results are presented in Table 4.

TABLE 4

Extraction yield for phloroglucinol (20 and 200 μg · ml$^{-1}$) and for resorcinol (200 μg · ml$^{-1}$), extracted with ethyl acetate, according to the method described

| Product | Phloroglucinol | | Resorcinol (EI) |
|---------|----------------|---|------------------|
| Concentration of phloroglucinol or of resorcinol in the culture medium (μg · ml$^{-1}$) | 20 | 200 | 200 |
| YLD (%) | 76 | 89 | 82 |

1.2.2. Development of a UPLC/UV and UPLC/Mass Analysis Method

A method of analysis by UPLC chromatography and UV (ultraviolet radiation) absorbance measurement was developed. The extract is chromatographed on a pentafluorophenyl propyl (PFP) column having the dimensions 100×2.1 mm, 1.8 μm, according to a 0.1% HCOOH/ACN-0.1% HCOOH gradient. The phloroglucinol is detected by UV at 230 nm. A UPLC-mass spectrometry (UPLC/Mass) method was also developed.

The quantification is carried out using a range of 20 to 200 μg·ml$^{-1}$ of phloroglucinol diluted in yeast culture medium (Yeast Extract 1%, BactoPeptone 2%) in the presence of a fixed amount of resorcinol, used as internal standard. The amount of phloroglucinol is determined by calculating the surface ratios of the phloroglucinol/resorcinol chromatography peaks.

Figure 2:
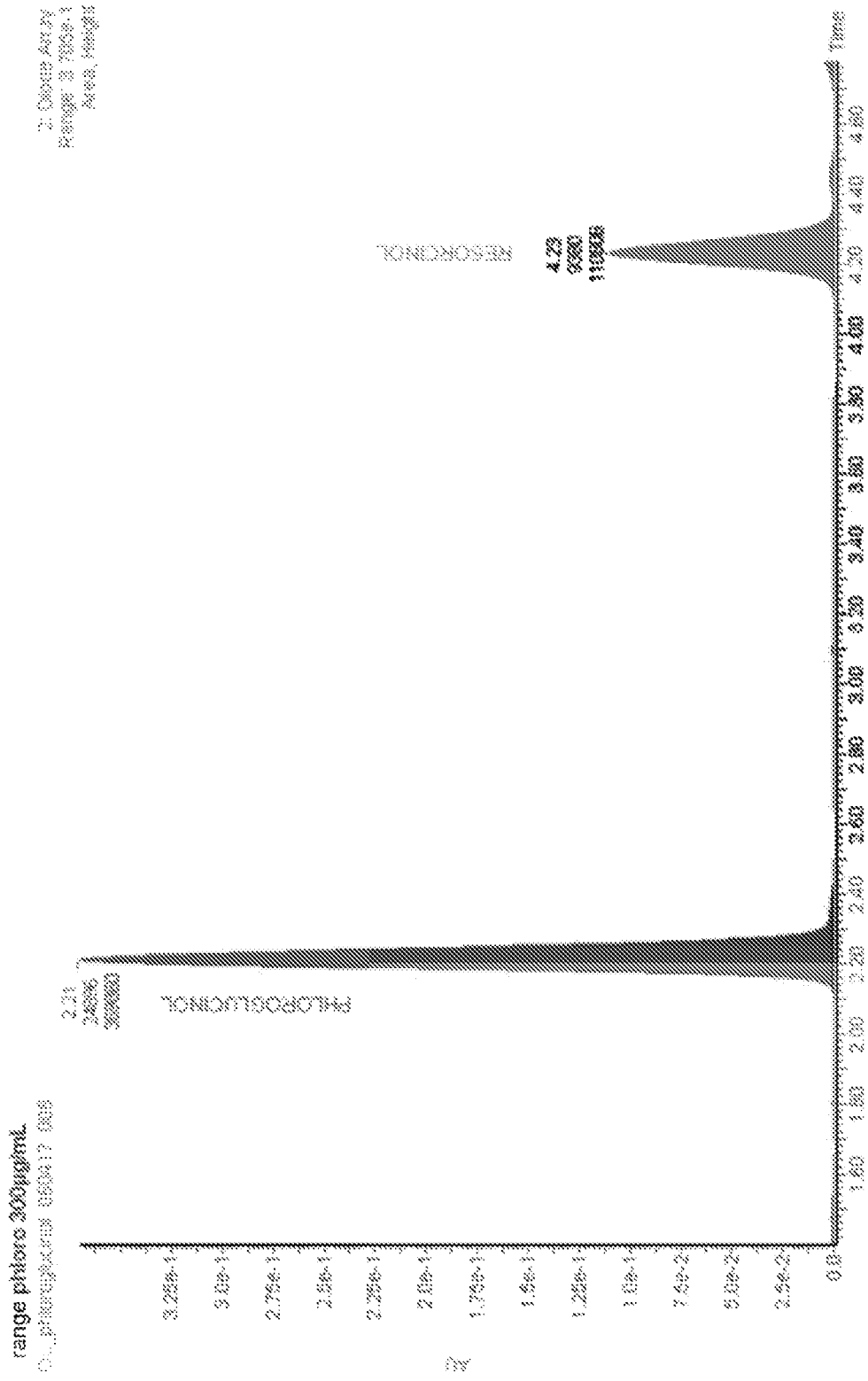
FIG. 2 presents an example of phloroglucinol/resorcinol separation on a propyl-pentafluorophenyl (PFP) column.

FIG. 2 presents an example of phloroglucinol/resorcinol chromatography peaks obtained on a PFP column.

This assay method thus makes it possible to reliably measure, qualitatively and quantitatively, the phloroglucinol present in a sample.

The UPLC-mass spectrometry (UPLC/mass) method makes it possible to assay the samples containing a phloroglucinol concentration ranging from 2 to 50 μg/ml.

Example 2

Reconstitution of an Active Form as Phloroglucinol Synthase of the PHLD.Aa Enzyme of *Aureococcus anophagefferens*

The first results of the activity tests carried out with the *Aureococcus anophagefferens* sequence, as annotated in the databases (denoted PHLD.Aa), identified in example 1 as a putative type III polyketide synthase, had not resulted in the production of phloroglucinol (see example 3 below).

A comparative analysis of the sequence of the corresponding PHLD.Aa gene was carried out in order to understand this absence of activity. This sequence was described following the annotation of the genome of the *Aureococcus anophagefferens* alga (version AURANDRAFT_25482 of the genomic sequence).

The comparative analysis of the sequence made it possible to demonstrate, surprisingly, that the protein sequence of the PHLD.Aa enzyme as annotated in the databanks is significantly shorter in its amino-terminal portion than the sequences of the other 3 enzymes or candidates. This result would thus suggest an error in the annotation of the genome.

A nucleic sequence encoding a protein sequence resembling the amino-terminal portion of the candidate gene PHLD.Sbi of *Sargassum binderi* was thus searched for in the version AURANDRAFT-25482 of the *A. anophagefferens* genome. For this, the protein sequence of the amino-terminal portion of the PHLD.Sbi protein was aligned with the sequence resulting from the translation of the 6 frames of the sequence contigs of the *A. anophagefferens* genome, using the Blast software. The result of this search is presented in FIG. 3.

Figure 3:
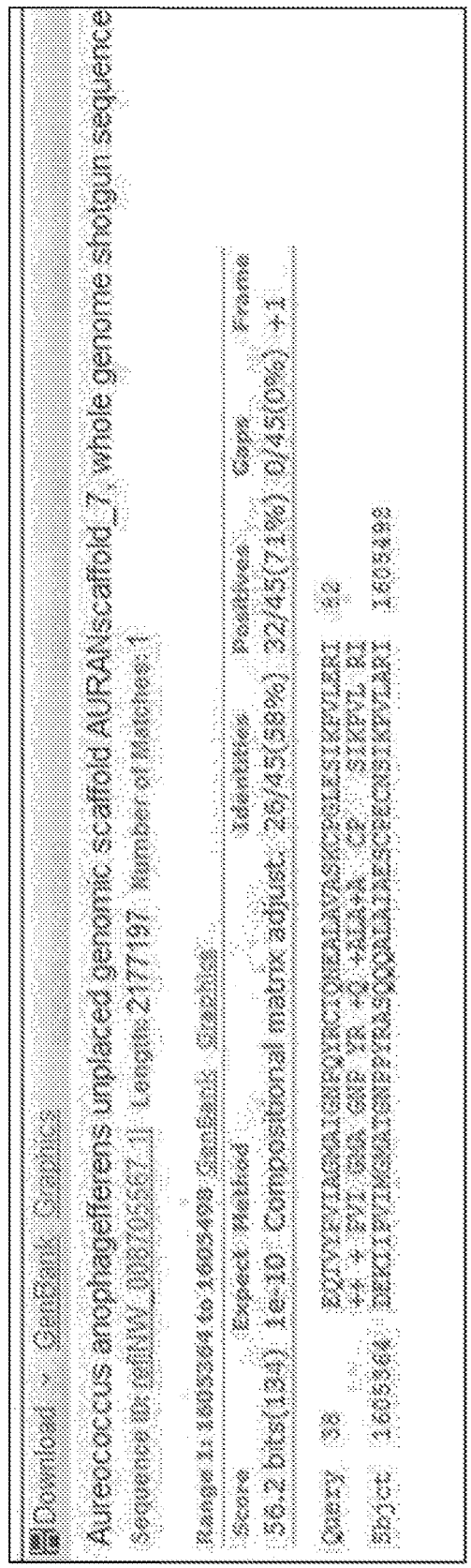
FIG. 3 shows the result of the Blast search of the N-terminal portion of PHLD.Sbi in the contigs of the *A. anophageferens* genome.

FIG. 3 shows that the *A. anophagefferens* genome indeed contains a nucleotide sequence encoding a peptide sequence very similar to the amino-terminal portion of the PKS1.Es and PHLD.Sbi genes.

Figure 4:
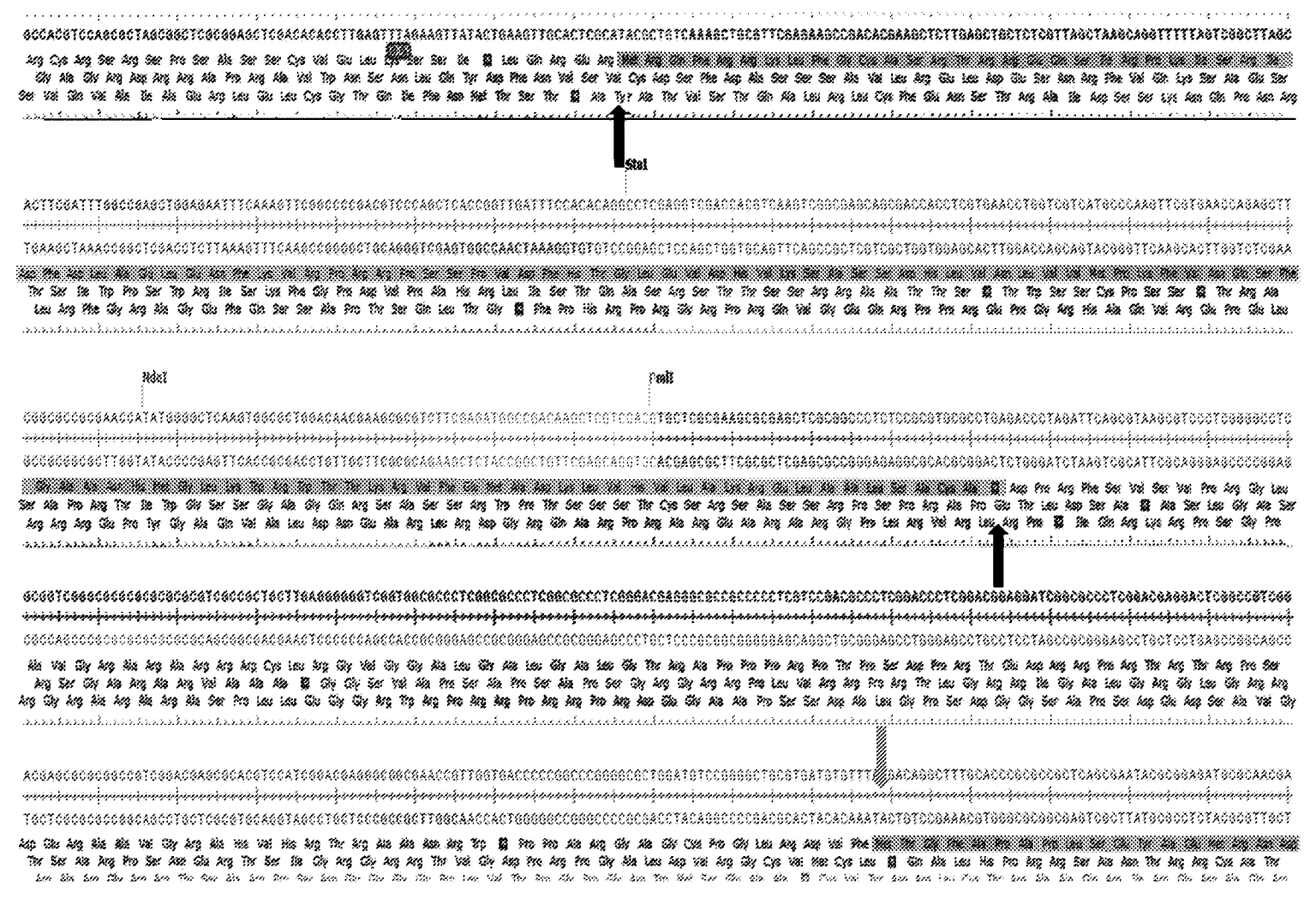

FIG. 4 shows the location of the *A. anophagefferens* genomic sequence encoding a peptide sequence homologous to the amino-terminal portion of PHLD.Sbi (sequence highlighted in light grey framed by 2 black arrows) located 5' of the sequence of the PHLD.Aa gene (dark grey arrow) as annotated in the genomic databanks. Thus, this sequence is positioned upstream of the 5' portion of the PHLD.Aa gene in the *A. anophagefferens* genome as annotated and is separated from the latter by a noncoding nucleotide sequence of approximately 300 base pairs.

The probability that this configuration is maintained for no reason in the *A. anophagefferens* genome is minute. It was therefore probable that this sequence of 300 base pairs corresponds either to an intron sequence, or to an error of assembly of the genomic sequence in the databanks. These results would suggest that the sequence of the PHLD.Aa enzyme consists in reality of the combination of these two peptide sequences that are encoded by the reconstituted sequence shown in FIG. 5.

Figure 5:
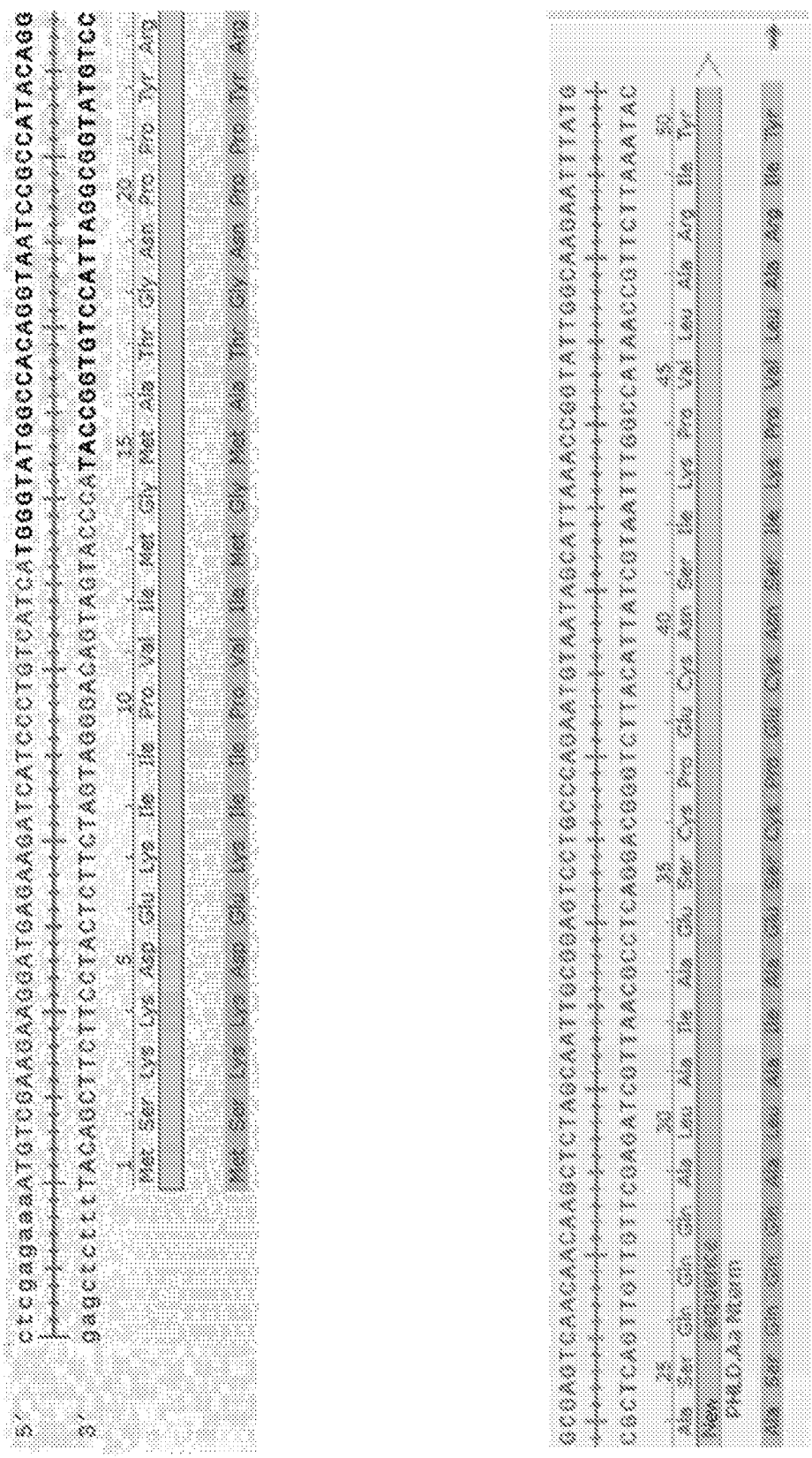
FIG. 5 shows the amino-terminal portion of the reconstituted peptide sequence of the PHLD-1.Aa enzyme.
Figure 5:
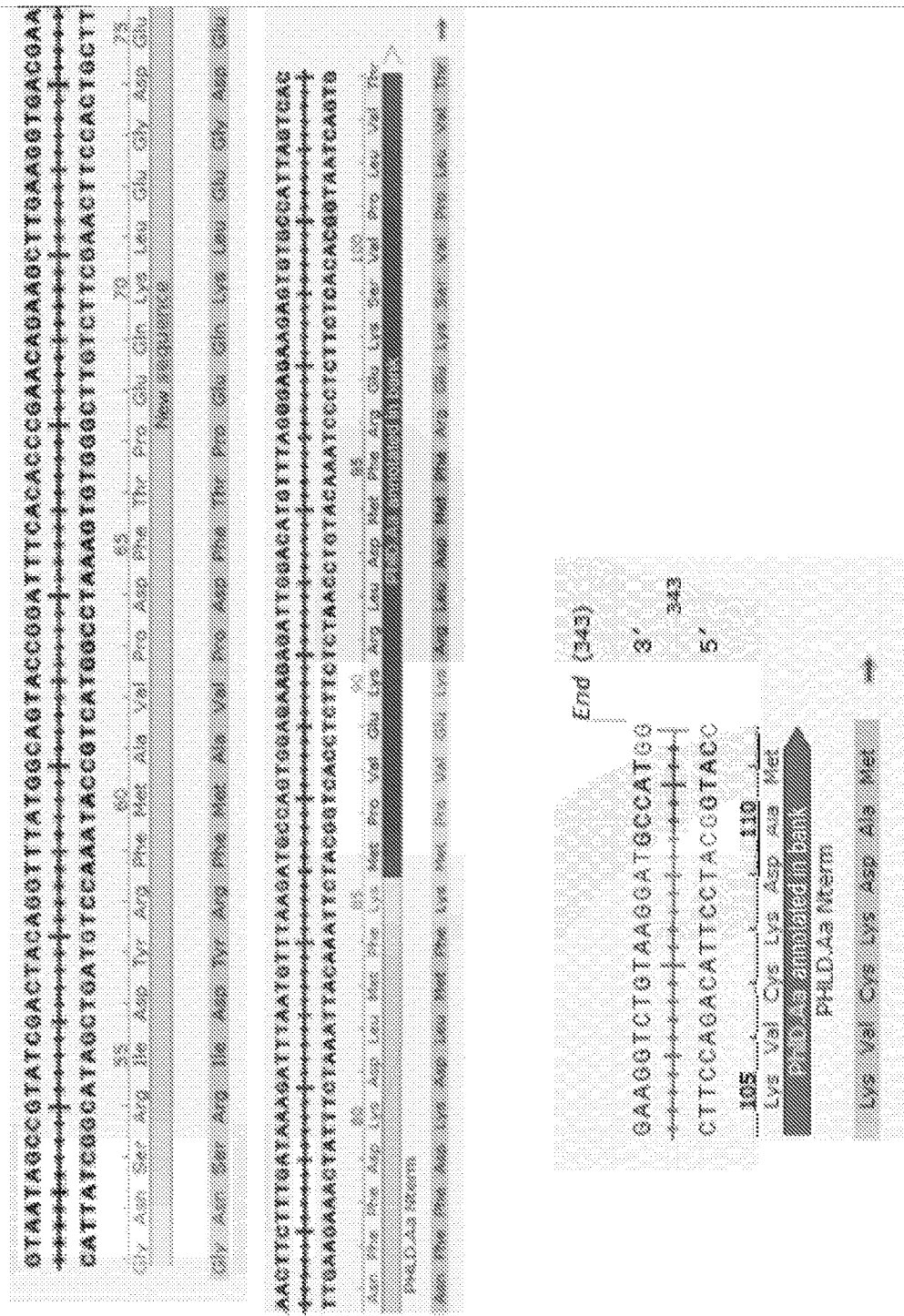

The complete sequence of the *A. anophagefferens* enzyme was thus reconstituted by the inventors by combining these two sequences so as to form the protein called PHLD-1.Aa. The junction of the two sequences resulted in the establishment of the PHLD-1.Aa peptide sequence having an amino-terminal portion similar to that of PHLD.Sbi (FIG. 5).

The alignment of the nucleotide sequence encoding the reconstituted PHLD-1.Aa enzyme with the sequences of the other PHLD candidate genes confirmed that the PHLD-1.Aa sequence is more similar to the other candidates identified in example 1 (data not shown).

Figure 6:
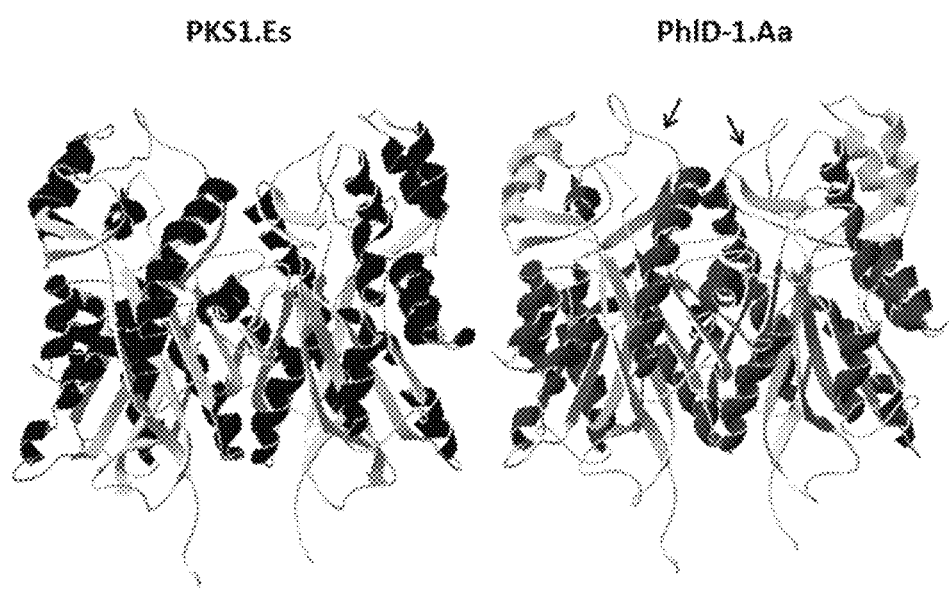
FIG. 6 shows the comparison between the three-dimensional (3D) structure of the PKS1.Es enzyme and the modelled structure of the reconstituted PHLD-1.Aa enzyme. The N-terminal portion identified by homology with the PHLD.Sbi sequence is represented in light grey (the arrows indicate the beginning of the N-terminal portion of each monomer).

The three-dimensional structure of the reconstituted PHLD-1.Aa enzyme was modelled, and was compared to that of the PKS1 enzyme of *E. siliculosus* (established by Meslet-Cladière et al., 2013). It is clearly apparent that the addition of the amino-terminal sequence identified here allows a much better juxtaposition of the structures of these two enzymes, the dimeric forms of which are represented by FIG. 6.

The PHLD-1.Aa enzyme was cloned under the control of the ADH2 promoter and the resulting gene construct was integrated at the URA3 locus of the W303 yeast strain (multicopy integration). The transformants obtained were cultured in the presence of 20 g.l$^{-1}$ of ethanol as carbon source and the phloroglucinol production was measured after 48 hours of culture at 30° C.

The results obtained show that the yeast cells expressing the reconstituted PHLD-1.Aa form produced significant amounts of phloroglucinol (about 200 mg.l$^{-1}$, see Example 3 below), unlike the yeast strains expressing the "truncated" PHLD.Aa form derived from the annotated genome. These results thus confirm that the PHLD.Aa sequence present in the databases is incomplete and that the identification, by the inventors, of an amino-terminal portion in the genomic sequence has made it possible to establish that the PHLD-1.Aa form from *A. anophagefferens* constitutes a new phloroglucinol synthase.

Example 3

Identification of New Functional Phloroglucinol Synthases 3.1. Expression of the Candidate Genes in the *Saccharomyces cerevisiae* Yeast In Multicopy Form The 2 candidate genes PHLD-1.Aa and PHLD.Sbi, and also the PHLD.Pf and PKS1.Es genes encoding the two phloroglucinol synthases identified to date and used as controls (see Table 1; shaded rows) and the candidate gene PHLD.Aa were synthesized by adapting the codons used for optimal expression in the *S. cerevisiae* yeast.

This codon adaptation was carried out in order to optimize the expression of these different genes in the yeast cells (these 5 synthetic genes encode proteins strictly identical to the proteins or putative proteins expressed by the organisms of origin). Each of these genes was placed under the control of the same yeast promoter ADH2 (pADH2) which allows their expression in particular when the culture medium contains ethanol as carbon source. The transcription terminator of the RPL3 yeast gene (tRPL3) was placed downstream of each of the 5 genes placed under the control of the ADH2 promoter.

Figure 7:
FIG. 7 shows an example of the structure of a gene unit constructed for a given candidate (PHLD.ii), making it possible to express the PHLD genes in the yeast *Saccharomyces cerevisiae*.

FIG. 7 shows an example of a gene unit thus constructed for a candidate or a given control (PHLD.ii).

The various gene units thus constructed were independently integrated at the URA3 locus of the genome of a wild-type strain of the *S. cerevisiae* yeast. The wild-type strain used is the commercial strain W303 (genotype: MATa, his3, leu2, trp1, ura3, ade-). The integration technique used allows the integration of a variable number of copies of each gene unit. For each construct, the number of copies of gene units integrated was determined by quantitative PCR according to the conventional Taqnnan method.

The yeast strains expressing various numbers of copies of each of the 3 PHLD.ii candidate genes or of the PHLD.Pf and PKS1.Es control genes described above were cultured in the presence of 20 g.l$^{-1}$ of ethanol as carbon source for 48 hours at 30° C. The 5 yeast strains independently obtained after transformation and integration, at the URA3 locus, of the gene units described above were thus analysed for their capacity to produce phloroglucinol. The W303 wild-type parental strain was cultured under the same conditions and used as a control.

Figure 8D:
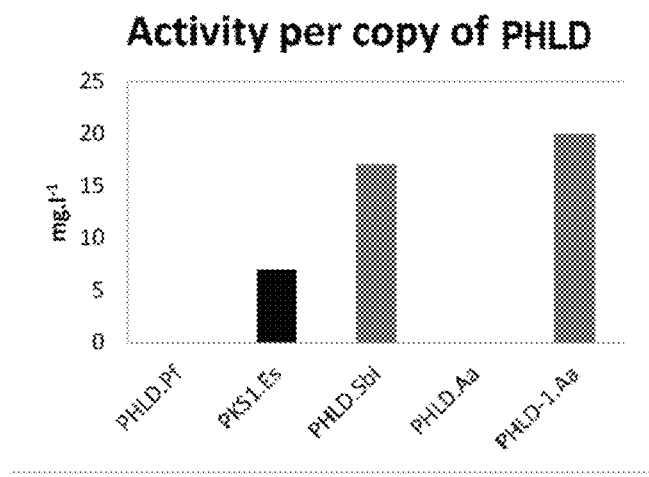
FIG. 8 shows the levels of phloroglucinol production in the yeast strains expressing the various PHLD.ii and PKS1.Es genes (several copies) under the control of the ADH2 promoter, after 48 hours of culture in a 24-well plate in the presence of 20 g.l$^{-1}$ of ethanol as carbon source at 30° C. (A) Summary of the various data measured. (B) Optical densities (OD) of the various cultures measured at 600 nm (OD$_{600}$), indicating the level of growth of each strain.

The optical densities (ODs) of the various cultures were measured at 600 nm (OD600), thus indicating the level of growth of each strain (FIGS. 8A and B).

The capacity of the various yeast strains expressing the various PHLD.ii genes, under the control of the ADH2 promoter, to synthesize phloroglucinol was tested using the extraction and assay method developed as described in section 1.2 above. The phloroglucinol production level (in mg.l$^{-1}$) was measured in the culture medium (FIGS. 8A and C).

FIG. 8 shows that all of the strains expressing different numbers of copies of the PHLD.Sbi, PHLD-1.Aa and PKS1.Es genes produce a significant amount of phloroglucinol which is excreted into the culture medium (FIGS. 8A, C and D). These results thus indicate that each of these 3 genes expresses a phloroglucinol synthase that is active in yeast.

Surprisingly, the results show that the PHLD.Aa candidate enzyme does not exhibit phloroglucinol synthase activity under the conditions tested. The inventors were able to demonstrate the fact that the PHLD.Aa protein as annotated in the databanks is significantly shorter in its amino-terminal portion than the other PHLDs (see example 2). The PHLD-1.Aa candidate enzyme exhibits, for its part, a significant phloroglucinol synthase activity under the conditions tested. These results show that the gene reconstituted and reannotated according to example 2 (PHLD-1.Aa) produces a PHLD phloroglucinol synthase that is functional in yeast.

Furthermore, as expected, no phloroglucinol production was measured in the W303 control parental strain (data not shown).

Thus, this functional study made it possible to identify two new phloroglucinol synthases, encoded respectively by the PHLD.Sbi and PHLD-1.Aa genes. This study reveals for the first time that the algae *S. binderi* and *A. anophagefferens* encode functional phloroglucinol synthases (PHLD.Sbi and PHLD-1.Aa). This study also reveals for the first time that the PKS1.ES enzyme is functional when it is expressed in a heterologous eukaryotic system, namely yeast.

This study also reveals, unexpectedly, that PHLD.Pf does not encode a phloroglucinol synthase that is functional in yeast. This result is surprising since the enzyme encoded by PHLD.Pf exhibits a phloroglucinol synthase activity demonstrated when it is expressed in *Escherichia coli* (Achkar et al., 2005).

3.2. Expression of the Candidate Genes in the *Saccharomyces cerevisiae* Yeast In the Form of a Single Copy The production of phloroglucinol by strains having integrated only a single copy of the PHLD.ii candidate genes selected and identified as being functional in yeast (see the results of the preceding section and FIG. 8) was also evaluated. The PKS1.Es gene encoding phloroglucinol synthase that is functional in yeast according to the results described in section 3.1 above was used as positive control.

Each of these genes was placed either under the control of the yeast promoter ADH2 (pADH2), which allows their expression in particular when the culture medium contains ethanol as carbon source, or under the control of the yeast promoter CCW12 (pCCW12), which allows their expression, in particular during glycolysis, when the culture medium contains glucose as carbon source. The transcription terminator of the RPL3 yeast gene (tRPL3) was placed downstream of each of the constructs.

The details of the various gene constructs produced is reported in FIG. 9.

The yeast strains expressing a single copy of PHLD or of PKS1 were cultured in the presence of 20 g.l$^{-1}$ of ethanol as carbon source (constructs controlled by pADH2) or in the presence of 20 g.l$^{-1}$ of glucose (constructs controlled by pCCW12) for 48 hours at 30° C. (FIGS. 10 and 11).

The strains were cultured and analysed for their capacity to produce phloroglucinol.

The optical densities of the various cultures were measured at 600 nm (indicating the level of growth of each strain; FIGS. 10A and 10B, FIGS. 11A and 11B) and the phloroglucinol production (in nng.l$^{-1}$) was measured in the culture medium, for 2 independent transformants for each construct (FIGS. 10A and 10C, FIGS. 11A and 11C).

Figures 10A, 10B:
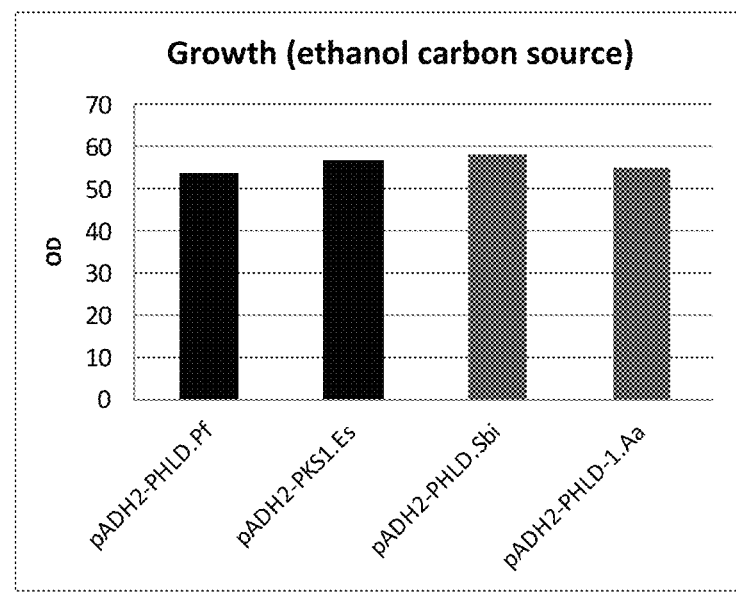
Figures 10C, 11A:
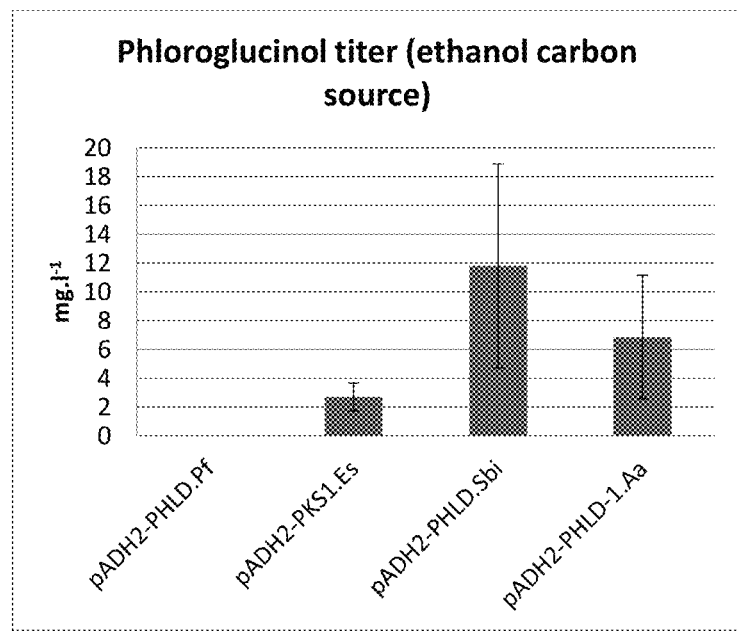
Figure 11B:
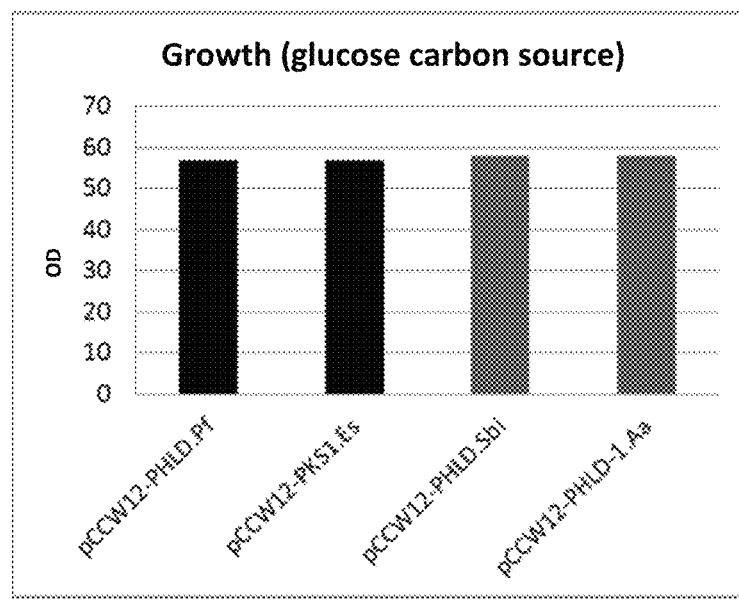

FIG. 10 shows that the strains expressing a single copy of the PHLD.Sbi and PHLD-1.Aa genes under the control of the ADH2 promoter synthesize a measurable and significant amount of phloroglucinol which is excreted into the culture medium (FIGS. 10A and 10C).

Figure 11C:
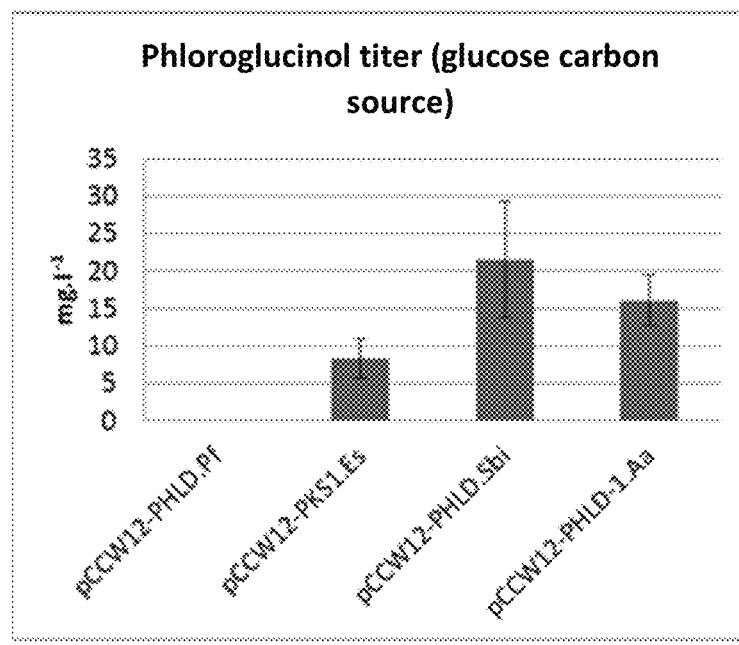

For the cultures carried out in the presence of glucose as carbon source, the strains expressing a single copy of the PKS1.Es, PHLD.Sbi and PHLD-1.Aa genes under the control of the CCW12 promoter all synthesize phloroglucinol, but in a higher amount than for the cultures carried out in the presence of ethanol as carbon source (FIGS. 11A and 11C).

The results obtained above confirm the results obtained in the strains containing several copies of the phloroglucinol synthases described in section 3.1 above. Thus, the expression of the PHLD.Sbi and PHLD-1.Aa candidate enzymes results in the significant production of phloroglucinol by the yeast cells. These results show that these genes encode phloroglucinol synthases and that these phloroglucinol synthases are active in yeast cells.

In addition, these results show that the levels of phloroglucinol production are high even when a single copy of the gene encoding the phloroglucinol synthase is expressed. In addition, the activity measured in the strains comprising a single copy is comparable to the obtained activity measured and divided by the number of copies of each gene inserted (thus related back to 1 copy of each gene) in the strains comprising the PHLD.ii genes in multicopy form.

These results are the first demonstrations of the existence of a phloroglucinol synthase activity in the algae *S. binderi* and *A. anophagefferens*.

3.3. Additional Observations

The study carried out by the inventors and reported here made it possible to identify 2 new enzymes having a phloroglucinol synthase activity in algae (PHLD.Sbi and PHLD-1.Aa).

The results also demonstrate for the first time and unequivocally that it is possible to synthesize phloroglucinol in yeast cells.

It is important to note that the phloroglucinol synthesized is more than 95% secreted into the culture medium by the yeast cells. This particularly efficient secretion is very favourable to the implementation of a phloroglucinol bioproduction process.

Finally, the enzymes identified by the inventors are original in terms of species of origin and in terms of protein sequences.

Indeed, it is shown for the first time that algae belonging to the *Sargassum* and *Aureococcus* genera encode functional phloroglucinol synthases. This discovery is all the more surprising since the previous attempts to identify phloroglucinol synthase in *Sargassum* sp. failed (Baharum et al., 2011).

In addition, the nucleic and protein sequences of the PHLD-1.Aa enzyme of *A. anophagefferens* are described herein for the first time.

LITERATURE REFERENCES

Achkar J et al., (2005) "Biosynthesis of phloroglucinol" *J. Am. Chem. Soc.* 127:5332-5333.

Baharum H. et al., (2011) "Molecular Cloning, Modeling, and Site-Directed Mutagenesis of Type III Polyketide Synthase from *Sargassum binderi*" *Mar. Biotechnol.* 13:845-856.

Meslet-Cladière L, Delage L, Leroux C J, Goulitquer S, Leblanc C, Creis E, Gall E A, Stiger-Pouvreau V, Czjzek M, and Potin P. (2013) "Structure/function analysis of a type III polyketide synthase in the brown alga *Ectocarpus siliculosus* reveals a biochemical pathway in phlorotannin monomer biosynthesis." *Plant Cell.* 25:3089-3103.

Zha W, Rubin-Pitel S B and Zhao H. (2006) "Characterization of the substrate specificity of PHLD, a type III polyketide synthase from *Pseudomonas fluorescens.*" *J. Biol. Chem.* 281:32036-32047.

The invention claimed is:

1. A method comprising:
producing phloroglucinol with at least one polypeptide with phloroglucinol synthase activity, and a suitable substrate selected from the group consisting of a carbon source and a thioester;
wherein the at least one polypeptide is selected from type III polyketide synthases of algae and comprises at least one amino acid sequence selected from the group consisting of a sequence having at least 85% identity with SEQ ID NO: 3 and a sequence having 100% identity with SEQ ID NO: 1.

2. The method according to claim 1, wherein said polypeptide is type III polyketide synthases of eukaryotic algae.

3. The method according to claim 1, wherein said polypeptide is type III polyketide synthases of ochrophyte algae.

4. The method according to claim 3, wherein said ochrophyte algae are selected from the group consisting of Aureococcus sp. and Sargassum sp.

5. A recombinant isolated polypeptide with phloroglucinol synthase activity comprising at least one amino acid sequence having at least 85% identity with the sequence SEQ ID NO: 3.

6. An isolated nucleic acid molecule encoding the isolated polypeptide according to claim 5.

7. An isolated nucleic acid molecule comprising:
at least one nucleic acid sequence encoding a polypeptide selected from type III polyketide synthases of algae; and
a promoter controlling the expression of said at least one nucleic acid sequence,
wherein the polypeptide comprises at least one amino acid sequence selected from the group consisting of a sequence having at least 85% identity with SEQ ID NO: 3 and a sequence having 100% identity with SEQ ID NO: 1.

8. The isolated nucleic acid molecule according to claim 7, wherein the promoter is an exogenous promoter.

9. An isolated nucleic acid molecule comprising:
at least one nucleic acid sequence encoding a polypeptide selected from type III polyketide synthases of algae; and
a terminator controlling the expression of said at least one nucleic acid sequence,
wherein the polypeptide comprises at least one amino acid sequence selected from the group consisting of a sequence having at least 85% identity with SEQ ID NO: 3 and a sequence having 100% identity with SEQ ID NO:1.

10. The isolated nucleic acid molecule according to claim 9, wherein the terminator is an exogenous terminator.

11. The isolated nucleic acid molecule according to claim 7 further comprising a transcription terminator for said at least one nucleic acid sequence.

12. A vector comprising at least one nucleic acid molecule according to claim 6.

13. A host cell comprising at least one nucleic acid molecule according to claim 6.

14. A host cell comprising at least one vector according to claim 12.

15. The host cell according to claim 13, wherein said host cell is a microorganism selected from the group consisting of bacteria, yeast, fungi, algae and cyanobacteria.

16. The host cell according to claim 13, wherein at least one copy of said at least one nucleic acid molecule is integrated into the genome of said host cell.

17. The host cell according to claim 14, wherein said host cell is a microorganism selected from the group consisting of bacteria, yeast, fungi, algae and cyanobacteria.

18. The host cell according to claim 14, wherein at least one copy of said at least one nucleic acid molecule is integrated into the genome of said host cell.

19. A method for producing phloroglucinol comprising:
 (i) contacting, with a suitable substrate, a host cell expressing at least one polypeptide with phloroglucinol synthase activity, wherein said at least one polypeptide is selected from type III polyketide synthases of algae and comprises at least one amino acid sequence selected from the group consisting of a sequence having at least 85% identity with SEQ ID NO: 3 and a sequence having 100% identity with SEQ ID NO:1, and wherein the suitable substrate is a carbon source; and
 (ii) growing, in vitro, the host cell of step (i) under conditions which allow the growth of said host cell, the expression of the nucleic acid molecule contained in said host cell, or both the growth of said host cell and the expression of the nucleic acid molecule contained in said host cell, so as to produce phloroglucinol.

20. A method for producing phloroglucinol comprising:
 (i) contacting, with a suitable substrate, at least one polypeptide with phloroglucinol synthase activity, wherein the at least polypeptide is selected from type III polyketide synthases of algae and comprises at least one amino acid sequence selected from the group consisting of a sequence having at least 85% identity with SEQ ID NO: 3 and a sequence having 100% identity with SEQ ID NO: 1, and wherein the suitable substrate is a thioester; and
 (ii) incubating the mixture resulting from step (i) under conditions suitable for producing phloroglucinol.

* * * * *

SEQUENCE LISTING

<160> NUMBER OF SEQ ID NOS: 9

<210> SEQ ID NO 1
<211> LENGTH: 413
<212> TYPE: PRT
<213> ORGANISM: Sargassum binderi

<400> SEQUENCE: 1

```
Met Ser Ser Ala Ala Val Ala Met Leu Ala Asp Pro Thr Val Gln Ile
1               5                   10                  15

Ala Leu Ala Cys Ile Val Leu Ser Leu Ile Val Val Phe Arg Ser Tyr
            20                  25                  30

Arg Lys Gly Lys Asp Glu Gln Thr Val Tyr Pro Val Ile Ala Gly Met
        35                  40                  45

Ala Ile Gly Asn Pro Gln Tyr Arg Cys Thr Gln Asp Gln Ala Leu Thr
    50                  55                  60

Val Ala Gln Lys Cys Pro Gly Val Glu Ser Val Lys Pro Val Leu Glu
65                  70                  75                  80

Arg Ile Tyr Gly Asn Ser Arg Ile Gly Ser Arg Tyr Phe Ala Val Pro
                85                  90                  95

Asp Phe Thr Pro Asn Gln Ala Ala Lys Gly Asp Pro Met Phe Phe Pro
            100                 105                 110

Ala Asp Gly Ser Phe Glu Val Pro Val Asp Thr Arg Leu Asp Lys Phe
        115                 120                 125

Lys Glu Lys Ala Val Pro Leu Val Ser Asp Val Ala Arg Arg Ala Ile
    130                 135                 140

Lys Glu Ala Gly Ile Asp Val Ser Asp Val Ser Lys Leu Val Val Val
145                 150                 155                 160

Ser Ser Thr Gly Phe Leu Gly Pro Gly Leu Asp Cys Glu Leu Ile Lys
                165                 170                 175

Asn Leu Gly Leu Thr Arg Ser Val Asp Arg Thr Leu Ile Gly Phe Met
            180                 185                 190

Gly Cys Ala Ala Ala Met Asn Gly Phe Arg Asn Ala Asn Asp Phe Val
        195                 200                 205

Thr Ala Asn Pro Gly Lys Tyr Ala Leu Met Ile Cys Val Glu Leu Ser
    210                 215                 220

Ser Val His Thr Thr Phe Asp Asp Asn Ile Asn Asp Ala Ile Leu His
225                 230                 235                 240

Ala Ile Phe Ala Asp Gly Cys Ala Ala Ala Val Leu Lys Gly Val Arg
                245                 250                 255

Lys Glu Ala Pro Lys Gly Thr Leu Ala Ile Val Asp Asn His Ala Trp
            260                 265                 270

Leu Met Glu Gly Thr Glu Asp Gly Ile Thr Leu Ala Ile Lys Pro Asn
        275                 280                 285

Gly Ile Thr Cys Thr Leu Ser Lys Phe Leu Pro Gln Tyr Ile Ala Lys
    290                 295                 300

Asn Ile Ala Phe Phe Ala Asp Gly Phe Leu Lys Lys His Asn Leu Gly
305                 310                 315                 320

Arg Asp Asp Val Asp Phe Trp Cys Val His Pro Gly Gly Arg Arg Ile
                325                 330                 335

Ile Glu Glu Ala Gln Asn Gly Leu Gly Leu Thr Glu Ala Gln Thr Ala
            340                 345                 350

Asp Ser Trp Ala Val Leu Ala Glu Tyr Gly Asn Met Leu Ser Pro Ser
        355                 360                 365
```

```
Val Met Phe Val Leu Ser Arg Val Phe Lys Arg His Asn Ala Ala Leu
        370                 375                 380

Ala Gln Gly Lys Pro Gly Tyr Gln Thr Gly Met Ala Phe Ser Phe Ser
385                 390                 395                 400

Pro Gly Val Gly Ala Glu Gly Ile Leu Leu Arg Gln Ile
                405                 410

<210> SEQ ID NO 2
<211> LENGTH: 297
<212> TYPE: PRT
<213> ORGANISM: Aureococcus anophagefferens

<400> SEQUENCE: 2

Met Pro Val Glu Lys Arg Leu Asp Met Phe Arg Glu Lys Ser Val Pro
1               5                   10                  15

Leu Val Thr Lys Val Cys Lys Asp Ala Met Ala Asp Ala Gly Ile Asp
            20                  25                  30

Val Glu Gln Ile Gly Lys Leu Val Val Ser Ser Thr Gly Phe Leu
        35                  40                  45

Gly Pro Gly Leu Asp Ala Glu Leu Ile Lys Thr Leu Gly Leu Trp Arg
50                  55                  60

Gly Val Asp Arg Ser Leu Ile Gly Phe Met Gly Cys Ala Ala Ala Met
65                  70                  75                  80

Asn Gly Phe Arg Val Ala Asn Asp Phe Ala Met Ser His Pro Gly Lys
                85                  90                  95

Met Ala Leu Met Val Cys Val Glu Ile Ser Ser Val His Thr Thr Phe
            100                 105                 110

Asp Asp Asn Val Asn Asp Ala Ile Leu His Ala Ile Phe Ala Asp Gly
        115                 120                 125

Cys Ala Ala Val Ile Ser Gly Glu Lys Pro Gly Ser Ala Ala Ala
    130                 135                 140

Lys Gly Lys Phe Gly Ile Val Asp Thr His Gly Trp Leu Met Glu Gly
145                 150                 155                 160

Thr Glu Asp Gly Ile Thr Leu Ser Ile Asn Glu Asn Gly Ile Ser Cys
                165                 170                 175

Ile Leu Ser Lys Tyr Leu Pro Gln Tyr Ile Ala Lys Asn Met Ala Gly
            180                 185                 190

Tyr Val Asp Ser Phe Leu Gly Met His Gly Leu Gln Lys Thr Asp Met
        195                 200                 205

Asp Phe Trp Ala Ile His Pro Gly Gly Arg Arg Ile Ile Glu Glu Ala
210                 215                 220

Gln Asn Gly Leu Gly Leu Ser Glu Glu Gln Ala Lys Tyr Ser Trp Thr
225                 230                 235                 240

Val Leu Ser Gln Tyr Gly Asn Met Leu Ser Pro Ser Val Met Phe Val
                245                 250                 255

Leu Glu Leu Ile Leu Asn Asp His Lys Lys Ala Leu Ala Lys Gly Glu
            260                 265                 270

Arg Gly Leu Lys Gln Gly Ile Ala Phe Ser Phe Ser Pro Gly Val Gly
        275                 280                 285

Ala Glu Gly Ile Leu Ile Asn Val Met
    290                 295

<210> SEQ ID NO 3
<211> LENGTH: 382
<212> TYPE: PRT
<213> ORGANISM: Aureococcus anophagefferens
```

<400> SEQUENCE: 3

```
Met Ser Lys Lys Asp Glu Lys Ile Ile Pro Val Ile Met Gly Met Ala
1               5                   10                  15

Thr Gly Asn Pro Pro Tyr Arg Ala Ser Gln Gln Ala Leu Ala Ile
            20                  25                  30

Ala Glu Ser Cys Pro Glu Cys Asn Ser Ile Lys Pro Val Leu Ala Arg
        35                  40                  45

Ile Tyr Gly Asn Ser Arg Ile Asp Tyr Arg Phe Met Ala Val Pro Asp
    50                  55                  60

Phe Thr Pro Glu Gln Lys Leu Glu Gly Asp Glu Asn Phe Phe Asp Lys
65                  70                  75                  80

Asp Leu Met Phe Lys Met Pro Val Glu Lys Arg Leu Asp Met Phe Arg
                85                  90                  95

Glu Lys Ser Val Pro Leu Val Thr Lys Val Cys Lys Asp Ala Met Ala
            100                 105                 110

Asp Ala Gly Ile Asp Val Glu Gln Ile Gly Lys Leu Val Val Val Ser
        115                 120                 125

Ser Thr Gly Phe Leu Gly Pro Gly Leu Asp Ala Glu Leu Ile Lys Thr
    130                 135                 140

Leu Gly Leu Trp Arg Gly Val Asp Arg Ser Leu Ile Gly Phe Met Gly
145                 150                 155                 160

Cys Ala Ala Ala Met Asn Gly Phe Arg Val Ala Asn Asp Phe Ala Met
                165                 170                 175

Ser His Pro Gly Lys Met Ala Leu Met Val Cys Val Glu Ile Ser Ser
            180                 185                 190

Val His Thr Thr Phe Asp Asp Asn Val Asn Asp Ala Ile Leu His Ala
    195                 200                 205

Ile Phe Ala Asp Gly Cys Ala Ala Val Ile Ser Gly Glu Lys Pro
210                 215                 220

Gly Ser Ala Ala Ala Lys Gly Lys Phe Gly Ile Val Asp Thr His Gly
225                 230                 235                 240

Trp Leu Met Glu Gly Thr Glu Asp Gly Ile Thr Leu Ser Ile Asn Glu
                245                 250                 255

Asn Gly Ile Ser Cys Ile Leu Ser Lys Tyr Leu Pro Gln Tyr Ile Ala
            260                 265                 270

Lys Asn Met Ala Gly Tyr Val Asp Ser Phe Leu Gly Met His Gly Leu
        275                 280                 285

Gln Lys Thr Asp Met Asp Phe Trp Ala Ile His Pro Gly Gly Arg Arg
    290                 295                 300

Ile Ile Glu Glu Ala Gln Asn Gly Leu Gly Leu Ser Glu Gln Ala
305                 310                 315                 320

Lys Tyr Ser Trp Thr Val Leu Ser Gln Tyr Gly Asn Met Leu Ser Pro
                325                 330                 335

Ser Val Met Phe Val Leu Glu Leu Ile Leu Asn Asp His Lys Lys Ala
            340                 345                 350

Leu Ala Lys Gly Glu Arg Gly Leu Lys Gln Gly Ile Ala Phe Ser Phe
        355                 360                 365

Ser Pro Gly Val Gly Ala Glu Gly Ile Leu Ile Asn Val Met
    370                 375                 380
```

<210> SEQ ID NO 4
<211> LENGTH: 1149
<212> TYPE: DNA

<213> ORGANISM: Aureococcus anophagefferens

<400> SEQUENCE: 4

| | |
|---|---|
| atgtcgaaga aggatgagaa gatcatccct gtcatcatgg gtatggccac aggtaatccg | 60 |
| ccatacaggg cgagtcaaca acaagctcta gcaattgcgg agtcctgccc agaatgtaat | 120 |
| agcattaaac cggtattggc aagaatttat ggtaatagcc gtatcgacta caggtttatg | 180 |
| gcagtaccgg atttcacacc cgaacagaag cttgaaggtg acgaaaactt ctttgataaa | 240 |
| gatttaatgt ttaagatgcc agtggagaag agattggaca tgtttaggga aagagtgtg | 300 |
| ccattagtca cgaaggtctg taaggatgcc atggcagacg ctggtataga cgttgaacag | 360 |
| attggcaaac ttgtcgtggt atcatcaact ggcttcttag gccctggact agatgcggag | 420 |
| ttaattaaga cacttggact ttggcgtggt gttgaccggt ctctgattgg attcatgggt | 480 |
| tgtgcggcgg ccatgaacgg ttttcgggtt gctaatgatt tcgccatgtc ccacccggga | 540 |
| aagatggccc taatggtttg cgtcgaaata tcctctgtgc ataccacatt cgatgataac | 600 |
| gtaaatgatg caatacttca tgcgatcttc gccgatggat gtgcagccgc agtaaatatcg | 660 |
| ggagagaagc caggttctgc ggcagcgaaa ggcaaattcg gaatcgtcga tacgcatggt | 720 |
| tggctcatgg aaggcacaga agatgggata accctgtcta tcaatgaaaa tggtatatca | 780 |
| tgcatcttga gtaagtatct accacagtat attgcaaaga catggcagg ttacgtagat | 840 |
| agtttcctag gatgcatgg attacagaag acagatatg atttctgggc tattcaccc | 900 |
| ggcggccgca gaattataga ggaagcgcag aacggtttgg gtttatccga ggagcaggcg | 960 |
| aagtattctt ggactgttct tagtcagtat ggtaatatgt tgtcacctag cgtgatgttt | 1020 |
| gtgttagaac tgatccttaa tgaccacaag aaggcactgg caaagggaga gcgcggttta | 1080 |
| aagcaaggta tcgcatttag cttctcaccg ggtgttgggg ccgagggcat cctcattaat | 1140 |
| gttatgtaa | 1149 |

<210> SEQ ID NO 5
<211> LENGTH: 349
<212> TYPE: PRT
<213> ORGANISM: Pseudomonas fluorescens Pf5

<400> SEQUENCE: 5

```
Met Ser Thr Leu Cys Leu Pro His Val Met Phe Pro Gln His Lys Ile
1               5                   10                  15

Thr Gln Gln Met Val Asp His Leu Glu Asn Leu His Ala Asp His
            20                  25                  30

Pro Arg Met Ala Leu Ala Lys Arg Met Ile Ala Asn Thr Glu Val Asn
        35                  40                  45

Glu Arg His Leu Val Leu Pro Ile Asp Glu Leu Ala Val His Thr Gly
    50                  55                  60

Phe Thr His Arg Ser Ile Val Tyr Glu Arg Glu Ala Arg Gln Met Ser
65                  70                  75                  80

Ser Ala Ala Ala Arg Gln Ala Ile Glu Asn Ala Gly Leu Gln Ile Ser
                85                  90                  95

Asp Ile Arg Met Val Ile Val Thr Ser Cys Thr Gly Phe Met Met Pro
            100                 105                 110

Ser Leu Thr Ala His Leu Ile Asn Asp Leu Ala Leu Pro Thr Ser Thr
        115                 120                 125

Val Gln Leu Pro Ile Ala Gln Leu Gly Cys Val Ala Gly Ala Ala Ala
    130                 135                 140
```

Ile Asn Arg Ala Asn Asp Phe Ala Arg Leu Asp Ala Arg Asn His Val
145                 150                 155                 160

Leu Ile Val Ser Leu Glu Phe Ser Ser Leu Cys Tyr Gln Pro Asp Asp
            165                 170                 175

Thr Lys Leu His Ala Phe Ile Ser Ala Ala Leu Phe Gly Asp Ala Val
            180                 185                 190

Ser Ala Cys Val Leu Arg Ala Asp Asp Gln Ala Gly Gly Phe Lys Ile
            195                 200                 205

Lys Lys Thr Glu Ser Tyr Phe Leu Pro Lys Ser Glu His Tyr Ile Lys
        210                 215                 220

Tyr Asp Val Lys Asp Thr Gly Phe His Phe Thr Leu Asp Lys Ala Val
225                 230                 235                 240

Met Asn Ser Ile Lys Asp Val Ala Pro Val Met Glu Arg Leu Asn Tyr
                245                 250                 255

Glu Ser Phe Glu Gln Asn Cys Ala His Asn Asp Phe Phe Ile Phe His
            260                 265                 270

Thr Gly Gly Arg Lys Ile Leu Asp Glu Leu Val Met His Leu Asp Leu
        275                 280                 285

Ala Ser Asn Arg Val Ser Gln Ser Arg Ser Ser Leu Ser Glu Ala Gly
        290                 295                 300

Asn Ile Ala Ser Val Val Phe Asp Val Leu Lys Arg Gln Phe Asp
305                 310                 315                 320

Ser Asn Leu Asn Arg Gly Asp Ile Gly Leu Leu Ala Ala Phe Gly Pro
                325                 330                 335

Gly Phe Thr Ala Glu Met Ala Val Gly Glu Trp Thr Ala
            340                 345

<210> SEQ ID NO 6
<211> LENGTH: 381
<212> TYPE: PRT
<213> ORGANISM: Ectocarpus siliculosus

<400> SEQUENCE: 6

Met Ser Lys Asp Glu Gln Thr Val Tyr Pro Val Ile Ala Gly Met Ala
1               5                   10                  15

Ile Gly Asn Pro Gln Tyr Arg Cys Thr Gln Asn Glu Ala Leu Ala Val
            20                  25                  30

Ala Ser Lys Cys Pro Gly Leu Glu Ser Ile Lys Pro Val Leu Glu Arg
        35                  40                  45

Ile Tyr Gly Asn Ser Arg Ile Gly Ser Arg Tyr Phe Ala Val Pro Asp
    50                  55                  60

Phe Thr Pro Gly Arg Ala Ala Lys Gly Asp Pro Leu Phe Tyr Pro Ala
65                  70                  75                  80

Asp Gly Ser Tyr Gln Val Pro Val Asp Val Arg Leu Asp Lys Phe Lys
                85                  90                  95

Glu Lys Ala Val Pro Leu Val Ser Asp Val Ala Arg Arg Ala Ile Lys
            100                 105                 110

Glu Ala Gly Leu Asn Val Glu Asp Ile Ser Lys Leu Val Val Val Ser
        115                 120                 125

Ser Thr Gly Phe Leu Gly Pro Gly Leu Asp Cys Glu Leu Ile Lys Asn
    130                 135                 140

Leu Gly Leu Thr Arg Ser Val Asp Arg Thr Leu Ile Gly Phe Met Gly
145                 150                 155                 160

Cys Ala Ala Ala Met Asn Gly Phe Arg Asn Ala Asn Asp Tyr Val Thr
                165                 170                 175

```
Ala Asn Pro Gly Lys Tyr Ala Leu Met Ile Cys Val Glu Leu Ser Ser
            180                 185                 190

Val His Thr Thr Phe Asp Asp Asn Ile Asn Asp Ala Ile Leu His Ala
        195                 200                 205

Ile Phe Ala Asp Gly Cys Ala Ala Val Leu Lys Gly Ala Arg Lys
    210                 215                 220

Ser Glu Cys Pro Lys Gly Thr Leu Ala Ile Val Asp Asn His Ala Trp
225                 230                 235                 240

Leu Met Glu Gly Thr Glu Asp Gly Ile Thr Leu Ala Ile Lys Pro Asn
                245                 250                 255

Gly Ile Thr Cys Thr Leu Ser Lys Phe Leu Pro Gln Tyr Ile Ala Lys
                    260                 265                 270

Asn Ile Ala Phe Phe Ala Asp Gly Phe Leu Lys Lys His Lys Leu Gly
                275                 280                 285

Arg Asp Asp Val Asp Phe Trp Cys Val His Pro Gly Arg Arg Ile
    290                 295                 300

Ile Glu Glu Ala Gln Asn Gly Leu Gly Leu Ser Glu Gln Thr Ala
305                 310                 315                 320

Asp Ser Trp Ala Val Leu Gly Glu Tyr Gly Asn Met Leu Ser Pro Ser
                325                 330                 335

Val Met Phe Val Leu Ser Arg Val Phe Lys Arg His Asn Ala Ala Leu
                340                 345                 350

Ala Gln Gly Lys Pro Gly Tyr Gln Thr Gly Met Ala Phe Ser Phe Ser
                355                 360                 365

Pro Gly Val Gly Ala Glu Gly Ile Leu Leu Arg Gln Ile
    370                 375                 380

<210> SEQ ID NO 7
<211> LENGTH: 598
<212> TYPE: DNA
<213> ORGANISM: Saccharomyces cerevisiae

<400> SEQUENCE: 7
tatcttaact gatagtttga tcaaaggggc aaaacgtagg ggcaaacaaa cggaaaaatc      60
gtttctcaaa ttttctgatg ccaagaactc taaccagtct tatctaaaaa ttgccttatg     120
atccgtctct ccggttacag cctgtgtaac tgattaatcc tgcctttcta atcaccattc     180
taatgtttta attaagggat tttgtcttca ttaacggctt tcgctcataa aaatgttatg     240
acgttttgcc cgcaggcggg aaaccatcca cttcacgaga ctgatctcct ctgccggaac     300
accgggcatc tccaacttat aagttggaga ataagagaa tttcagattg agagaatgaa      360
aaaaaaaaaa aaaaaaggca gaggagagca tagaaatggg gttcactttt tggtaaagct     420
atagcatgcc tatcacatat aaatagagtg ccagtagcga cttttttcac actcgaaata     480
ctcttactac tgctctcttg ttgttttat cacttcttgt ttcttcttgg taaatagaat      540
atcaagctac aaaagcata caatcaacta tcaactatta actatatcgt aatacaca       598

<210> SEQ ID NO 8
<211> LENGTH: 998
<212> TYPE: DNA
<213> ORGANISM: Saccharomyces cerevisiae

<400> SEQUENCE: 8
aaccagggca agcaaaaata aagaaactt aatacgttat gccgtaatga agggctacca      60
aaaacgataa tctcaactgt aaacaggtac aatgcggacc cttttgccac aaaacataca    120
```

```
tcattcattg ccggaaaaag aaagaagtga agacagcagt gcagccagcc atgttgcgcc      180
aatctaatta tagatgctgg tgccctgagg atgtatctgg agccagccat ggcatcatgc      240
gctaccgccg gatgtaaaat ccgacacgca aaagaaaacc ttcgaggttg cgcacttcgc      300
ccacccatga accacacggt tagtccaaaa ggggcagttc agattccaga tgcgggaatt      360
agcttgctgc caccctcacc tcactaacgc tgcggtgtgc ggatacttca tgctatttat      420
agacgcgcgt gtcggaatca gcacgcgcaa gaaccaaatg ggaaaatcgg aatgggtcca      480
gaactgcttt gagtgctggc tattggcgtc tgatttccgt tttgggaatc ctttgccgcg      540
cgcccctctc aaaactccgc acaagtccca gaaagcggga aagaaataaa acgccaccaa      600
aaaaaaaaat aaaagccaat cctcgaagcg tgggtggtag gccctggatt atcccgtaca      660
agtatttctc aggagtaaaa aaaccgtttg ttttggaatt ccccatttcg cggccaccta      720
cgccgctatc tttgcaacaa ctatctgcga taactcagca aattttgcat attcgtgttg      780
cagtattgcg ataatgggag tcttacttcc aacataacgg cagaaagaaa tgtgagaaaa      840
ttttgcatcc tttgcctccg ttcaagtata taaagtcggc atgcttgata atctttcttt      900
ccatcctaca ttgttctaat tattcttatt ctcctttatt ctttcctaac ataccaagaa      960
attaatcttc tgtcattcgc ttaaacacta tatcaata                              998

<210> SEQ ID NO 9
<211> LENGTH: 300
<212> TYPE: DNA
<213> ORGANISM: Saccharomyces cerevisiae

<400> SEQUENCE: 9
gaagttttgt tagaaaataa atcatttttt aattgagcat tcttattcct attttattta       60
aatagtttta tgtattgtta gctacataca acagtttaaa tcaaattttc ttttcccaa      120 gtccaaaatg gaggtttatt ttgatgaccc gcatgcgatt atgttttgaa agtataagac      180
tacatacatg tacatatatt taaacatgta aacccgtcca ttatattgct tactttcttc      240 tttttgccg ttttgacttg gacctctggt ttgctatttc cttacaatct ttgctacaat      300
```